United States Patent [19]
Duggan et al.

[11] Patent Number: 5,264,420
[45] Date of Patent: Nov. 23, 1993

[54] FIBRINOGEN RECEPTOR ANTAGONISTS

[75] Inventors: Mark E. Duggan, Schwenksville; Melissa S. Egbertson, Ambler; Nathan Ihle, Perkasie; George D. Hartman, Lansdale; Laura M. Turchi, Broomall; David Whitman, Phoenixville, all of Pa.

[73] Assignee: Merck & Co., Inc., Rahway, N.J.

[21] Appl. No.: 860,748

[22] Filed: Mar. 25, 1992

Related U.S. Application Data

[63] Continuation-in-part of Ser. No. 750,646, Aug. 30, 1991, abandoned, which is a continuation-in-part of Ser. No. 650,389, Feb. 1, 1991, abandoned, which is a continuation-in-part of Ser. No. 589,145, Sep. 27, 1990, abandoned.

[51] Int. Cl.$^5$ .................... A61K 37/02; C07K 5/02; C07K 5/06; C07K 5/08
[52] U.S. Cl. ......................... 514/19; 514/18; 530/330; 530/331; 530/332; 546/201; 548/465
[58] Field of Search ............ 514/18, 19; 530/330, 530/331, 332; 546/201; 548/465

[56] References Cited

U.S. PATENT DOCUMENTS

| | | | |
|---|---|---|---|
| 4,122,255 | 10/1978 | Krapcho | 542/421 |
| 4,243,807 | 1/1981 | Friebe et al. | 546/232 |
| 4,622,331 | 11/1986 | Jozic | 514/331 |
| 4,772,585 | 9/1988 | Sarnoff et al. | 514/7 |
| 4,871,842 | 10/1989 | Sugihara et al. | 546/201 |
| 4,929,602 | 5/1990 | Harker et al. | 514/18 |
| 4,952,562 | 8/1990 | Klein et al. | 514/18 |
| 5,030,654 | 7/1991 | Barnish | 514/510 |

FOREIGN PATENT DOCUMENTS

| | | |
|---|---|---|
| 352249 | 1/1990 | European Pat. Off. . |
| 372486 | 6/1990 | European Pat. Off. . |
| 381033 | 8/1990 | European Pat. Off. . |
| 384362 | 8/1990 | European Pat. Off. . |
| 405537 | 1/1991 | European Pat. Off. . |
| 449079A | 10/1992 | European Pat. Off. . |
| 2207922 | 2/1989 | United Kingdom ............ 514/18 |

*Primary Examiner*—Jeffrey E. Russel
*Attorney, Agent, or Firm*—Richard S. Parr; Charles M. Caruso

[57] ABSTRACT

Fibrinogen receptor antagonists of the formula:

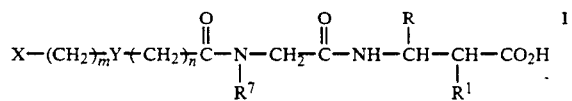

are disclosed for use in inhibiting the binding of fibrinogen to blood platelets and for inhibiting the aggregation of blood platelets.

9 Claims, No Drawings

FIBRINOGEN RECEPTOR ANTAGONISTS

CROSS REFERENCE

This is a continuation-in-part application of U.S. Ser. No. 07/750,646, filed Aug. 30, 1991, now abandoned, which is a continuation-in-part of U.S. Ser. No. 07/650,389, filed on Feb. 1, 1991, now abandoned, which is a continuation-in-part application of U.S. Ser. No. 07/589,145 filed on Sep. 27, 1990, now abandoned.

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

An interest in platelet inhibitors has reemerged as a result of a better understanding of the role of platelets and thrombosis in the pathogenesis of vascular disease, including unstable angina, acute myocardial infarction and stroke.

Platelets are cell-like anucleated fragments, found in the blood of all mammals, which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood.

Pierschbacher et al., U.S. Pat. No. 4,589,881, describes the sequence of an 11.5 kDal polypeptide fragment of fibronectin which embodies the cell-attachment-promoting activity of fibronectin.

Ruoslahti et al., U.S. Pat. No. 4,614,517, describes tetrapeptides which alter cell-attachment activity of cells to various substrates. FIG. 1 lists the polypeptides that were synthesized by Ruoslahti et al. in "determining the smallest peptide exhibiting cell attachment activity". Ruoslahti et al., Pat. No. 4,578,079, describes similar tetrapeptides having Ser substituted with Thr or Cys.

Pierschbacher et al., Proc. Natl. Acad. Sci. USA, Vol. 81, pp. 5985-5988, October, 1984, describe variants of the cell recognition site of fibronectin that retain attachment-promoting activity. Pierschbacher et. al. further assayed the cell attachment-promoting activities of a number of structures closely resembling the Arg-Gly-Asp-Ser peptide, and found "that the arginine, glycine, and aspartate residues cannot be replaced even with closely related amino acids, but that several amino acids can replace serine without loss of activity."

Ruoslahti et al., Science, Vol. 238, pp. 491–497, Oct. 23, 1987, discuss cell adhesion proteins. They specifically state that "elucidation of the amino acid sequence of the cell-attachment domain in fibronectin and its duplication with synthetic peptides establish the sequence Arg-Gly-Asp (RGD) as the essential structure recognized by cells in fibronectin".

Cheresh, Proc. Natl. Acad. Sci. USA, Vol. 84, pp. 6471–6475, September 1987, describes the Arg-Gly-Asp-directed adhesion receptor involved in attachment to fibrinogen and the von Willebrand Factor.

Adams et al., U.S. Pat. No. 4,857,508, describes tetrapeptides which inhibit platelet aggregation and the formation of a thrombus.

It is, therefore, an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

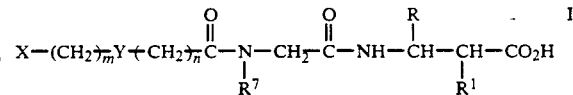

for use in inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

$$X-(CH_2)_m Y(CH_2)_n \overset{O}{\underset{\|}{C}}-N-CH_2-\overset{O}{\underset{\|}{C}}-NH-\overset{R}{\underset{|}{CH}}-\overset{}{\underset{R^1}{CH}}-CO_2H \qquad I$$
$$\phantom{X-(CH_2)_m Y(CH_2)_n C-}\underset{R^7}{|}$$

wherein:

X is $$-NR^2R^3, \quad -NH-\overset{NH}{\underset{\|}{C}}-NR^2R^3, \quad -\overset{NH}{\underset{\|}{C}}-NR^2R^3,$$

[cyclic structures with $R^2-N$, $R^4$, $(CH_2)_p$]

[bicyclic structures with A, B, $R^4$] or [bicyclic structures with A, B, $R^4$];

where A=N and B=—CH$_2$—, or A=

$$-\overset{}{\underset{|}{CH}}-$$

and B=NR$^2$;

Y is $$-\overset{R^6}{\underset{R^5}{\underset{|}{\overset{|}{C}}}}-, \quad -\overset{O}{\underset{\|}{C}}-NH-, \quad O, \quad N-R^6, \quad -\overset{O}{\underset{\|}{C}}-,$$

$$-S(O)_q-CH_2-, \quad -CH=CH-, \quad -C\equiv C-,$$

$$-SO_2NH-, \quad -\overset{NHR^6}{\underset{R^5}{\underset{|}{\overset{|}{C}}}}-, \quad \text{[phenyl]}, \quad \text{[Z heterocycle]},$$

$$-HN\overset{O}{\underset{\|}{C}}-, \quad -NHSO_2-, \quad \text{[cyclohexyl]};$$

R and R$^1$ are independently hydrogen, aryl, wherein aryl is defined as a five or six membered mono or polycyclic aromatic ring system containing 0, 1, 2, 3, or 4 heteroatoms selected from nitrogen, oxygen and sulfur, either unsubstituted or substituted, with one or more groups selected from hydroxyl, halogen, cyano, trifluoromethyl, $C_{1-3}$ alkoxy, $C_{1-5}$ alkylcarbonyloxy, $C_{1-5}$ alkoxycarbonyl, $C_{1-5}$ alkyl, amino$C_{1-5}$ alkyl, hydroxycarbonyl$C_{0-5}$ alkyl, or hydroxycarbonyl$C_{1-5}$ alkoxy, $C_{0-6}$alkyl, either unsubstituted or substituted, with one or more groups selected from halogen, hydroxyl, $C_{1-8}$alkylcarbonyl($C_{0-6}$alkyl)amino, aryl$C_{0-5}$alkylcarbonyl($C_{0-6}$alkyl) amino, aryl $C_{0-6}$ alkyloxy, $C_{1-10}$ alkyloxy, $C_{1-6}$ alkyloxycarbonyl $C_{0-6}$ alkyl, aryl $C_{0-6}$alkyloxycarbonyl-$C_{0-6}$ alkyl, $C_{0-6}$ alkylaminocarbonyl, $C_{1-6}$ alkylcarbonyloxy, $C_{3-8}$ cycloalkyl, aryl, oxo, amino, $C_{1-6}$ alkyl, $C_{1-6}$ alkylamino, aryl $C_{0-3}$ alkylamino, amino $C_{1-6}$ alkyl, $C_{0-5}$ alkylaminocarbonyl, aryl $C_{0-5}$ alkylaminocarbonyl, carboxy $C_{1-6}$ alkyl, carbo $C_{1-6}$ alkoxy $C_{1-6}$ alkyl, $C_{1-8}$ alkylsulfonyl ($C_{0-6}$ alkyl)amino, aryl $C_{0-8}$ alkylsulfonyl ($C_{0-6}$ alkyl)amino, $C_{0-8}$ alkylaminosulfonyl ($C_{0-8}$ alkyl)amino, aryl $C_{0-8}$ alkylaminosulfonyl($C_{0-8}$ alkyl)amino, $C_{0-8}$ alkylaminosulfonyl, aryl $C_{0-8}$ alkylaminosulfonyl, $C_{0-6}$ alkylaminocarbonyl ($C_{0-6}$ alkyl)amino, aryl $C_{0-6}$ alkylaminocarbonyl($C_{0-6}$ alkyl)amino, $C_{1-6}$ alkyloxycarbonylamino, aryl $C_{1-6}$ alkyloxycarbonylamino, $C_{1-8}$ alkylcarbonyl $C_{0-6}$ alkyl, aryl $C_{1-8}$ alkylcarbonyl $C_{0-6}$ alkyl, $C_{1-8}$ alkylsulfonyl $C_{0-6}$ alkyl, aryl $C_{1-8}$ alkylsulfonyl $C_{0-6}$ alkyl, $C_{1-8}$ alkyloxycarbonyl ($C_{0-6}$ alkyl) amino, aryl $C_{1-8}$ alkyloxycarbonyl ($C_{0-6}$ alkyl)amino, $C_{1-8}$ alkylaminocarbonyloxy, and aryl $C_{0-6}$ alkylaminocarbonyloxy, and wherein any of the above substituents may be independently substituted by one or more groups chosen from R$^5$;

R$^2$, R$^3$ and R$^4$ are independently hydrogen, $C_{1-12}$ alkyl, unsubstituted or substituted, with one or more $C_{1-6}$ alkyl groups, aryl$C_{0-4}$alkyl, or cyano provided that when R$^2$ and R$^3$ are independently cyano, X is $$-NH-\overset{NH}{\underset{\|}{C}}-NR^2R^3 \quad \text{or} \quad -\overset{NH}{\underset{\|}{C}}-NR^2R^3;$$

R$^5$ is hydrogen, $C_{1-6}$ alkyl, either unsubstituted or substituted, with one or more groups selected from $C_{1-6}$ alkyl, $C_{1-5}$ alkoxy, $C_{1-5}$ alkoxycarbonyl, hydroxycarbonyl$C_{0-4}$ alkyl, aryl, amino$C_{1-4}$alkyl, arylaminocarbonyl$C_{0-4}$ alkyl, $C_{1-4}$ alkyl sulfonyl, phenyl$C_{0-4}$ alkylsulfonyl, hydroxyl, or amino, hydroxycarbonyl, hydroxy or amino, provided that when R$^5$ is hydroxy or amino, R$^5$ is not attached to a carbon bearing a heteroatom;

R$^6$ is hydrogen, $C_{1-12}$ alkyl, unsubstituted or substituted, with one or more $C_{1-6}$ alkyl groups, aryl$C_{0-3}$ alkyl, $C_{1-4}$ alkyloxycarbonyl, aryl$C_{1-4}$ alkyloxycarbonyl, $C_{1-4}$ alkylaminocarbonyl, aryl$C_{1-4}$ alkylaminocarbonyl, $C_{2-5}$ alkoxy, oxycarbonyl$C_{2-5}$ alkyl, aminocarbonyl$C_{2-5}$ alkyl;

R$^7$ is hydrogen;

$C_{1-12}$ alkyl, unsubstituted or substituted, with one or more $C_{1-6}$ alkyl groups, $C_{3-7}$ cycloalkyl hydroxyl, hydroxycarbonyl, aminocarbonyl, oxo, aryl;

aryl; or $C_{3-7}$ cycloalkyl;
m is 1-10;
n is 0-9;
q is 0-2;
p is 1-6;
Z is O, N or S;
or the pharmaceutically acceptable salts thereof, or optical isomers thereof.

Preferred compounds of the present invention have the following formula:

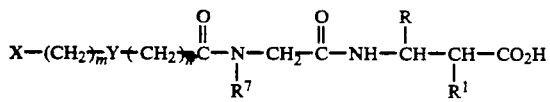

wherein:
X is

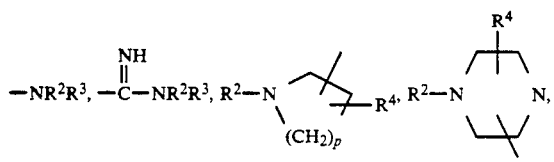

Y is

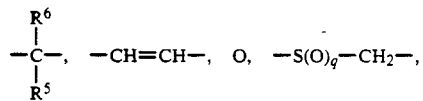

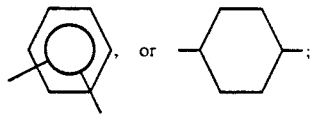

R and $R^1$ are independently chosen from phenyl, thiophene, imidazole, naphthyl, indole, indazole, thionaphthene, either unsubstituted or substituted, with hydroxy, halogen, hydroxycarbonyl $C_{0-5}$ alkyl, $C_{1-3}$alkyl, either unsubstituted or substituted, with one or more groups selected form aryl, aryloxy, $C_{1-10}$ alkoxy, $C_{0-5}$ alkylaminocarbonyl, aryl$C_{0-5}$ alkylaminocarbonyl, hydrogen, $C_{0-6}$alkyl, unsubstituted or substituted, with one or more groups selected from phenyl, thiophene, imidazole, naphthyl, indole, indazole, thionaphthene, $C_{1-6}$ alkylcarbonylamino, aryl $C_{0-6}$ alkylcarbonylamino, $C_{1-6}$ alkyloxycarbonyl, aryl $C_{1-6}$ alkyloxycarbonyl, amino, $C_{1-8}$ alkylsulfonylamino, aryl $C_{0-8}$ alkylsulfonylamino, $C_{1-8}$ alkylsulfonyl, aryl $C_{0-8}$ alkylsulfonyl, $C_{0-6}$ alkylaminocarbonylamino, and aryl $C_{0-6}$ alkylaminocarbonylamino;

$R^2$, $R^3$ and $R^4$ are independently hydrogen, or $C_{1-3}$alkyl, unsubstituted or substituted, with one or more $C_{1-6}$alkyl groups;

$R^5$ is,
hydrogen,
$C_{1-3}$alkyl, either unsubstituted or substituted, with one or more groups selected from amino, amino $C_{1-4}$alkyl, hydroxyl, aryl, arylaminocarbonyl $C_{0-4}$alkyl;

$R^6$ is, hydrogen, or
hydroxycarbonyl$C_{2-4}$alkyl;
$R^7$ is
hydrogen;
$C_{1-12}$ alkyl, unsubstituted or substituted, with one or more $C_{1-6}$ alkyl groups, $C_{3-7}$ cycloalkyl hydroxyl, hydroxycarbonyl, aminocarbonyl, oxo, aryl;
aryl; or
$C_{3-7}$ cycloalkyl;
m is 1-5;
n is 0-4;
q is 0-2;
p is 1-3;
Z is S;
or the pharmaceutically acceptable salts thereof, or optical isomers thereof.

More preferred compounds of the present invention have the following formula:

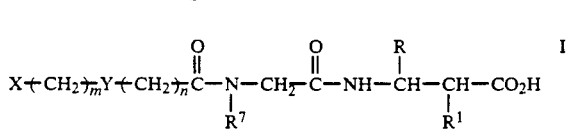

wherein
X is

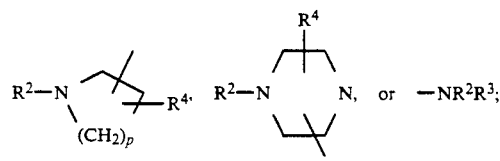

Y is

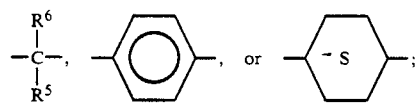

R and $R^1$ are independently chosen from phenyl, imidazole, indole, indazole, unsubstituted or substituted, with methyl, oxycarbonyl$C_{0-2}$ alkyl, hydrogen, $C_{0-6}$alkyl, unsubstituted or substituted, with one or more groups selected from phenyl, imidazole, indole, indazole, $C_{1-6}$ alkylcarbonylamino, aryl $C_{0-6}$ alkylcarbonylamino, $C_{1-8}$ alkylsulfonylamino, aryl $C_{0-8}$ alkylsulfonylamino, $C_{1-8}$ alkylsulfonyl, aryl $C_{0-8}$ alkylsulfonyl, $C_{0-6}$ alkylaminocarbonylamino, aryl $C_{0-6}$ alkylaminocarbonylamino;
$R^2$, $R^3$ and $R^4$ are hydrogen;
$R^5$ is, hydrogen or $C_{1-3}$ alkyl;
$R^6$ is, hydrogen;
$R^7$ is
hydrogen;
$C_{1-6}$ alkyl, unsubstituted or substituted, with one or more $C_{1-6}$ alkyl or aryl groups;
m is 1-5;
n is 0-3;
p is 3;
or the pharmaceutically acceptable salts thereof, or optical isomers thereof.

Preferred compounds of the invention are:
Pib-N-(benzyl)Gly-3(R)-(2-phenethyl)β-alanine,
Pib-N-(n-butyl)Gly-3(R)-(2-phenethyl)β-alanine, Pib-N-(i-Propyl)-3(R)-(2-phenethyl)β-alanine,
Pib-N-(2-phenethyl)Gly-3(R)-(2-phenethyl)β-alanine,
Pib-Gly-3(S)-[2-(indol-3-yl)ethyl]-β-alanine ethyl ester,
Pib-Gly-3(S)-[2-(indol-3-yl)-ethyl]β-alanine,
Pib-Gly-3,3-[(2-phenethyl),(methyl)]β-alanine,
Pib-Gly-3-[2-(hydroxy)ethyl]β-alanine,
Pib-Gly-3-[4-(hydroxy)butyl]β-alanine,
Pib-Gly-3-(phenoxymethyl)β-alanine,
Pib-Gly-3-[2-(imidazol-4-yl)ethyl]β-alanine,
Pib-Gly-3-[2-(3-benzylimidazol-4-yl)ethyl]β-alanine,
Pib-Gly-3(3-carboxypropyl)β-alanine,
Pib-Gly-3[2-(2-methylindol-3-yl)ethyl]β-alanine,
Pib-Gly-3(R)-(2-phenethyl)β-alanine,
Pib-Gly-3-[2-(indol-3-yl)ethyl]β-alanine,
Pib-Gly-3(R)-[2-(indol-3-yl)ethyl]β-alanine,
Pib-Gly-3(S)-[2-(indol-3-yl)ethyl]β-alanine,
Pib-Sar-3(R)-[2-(indol-3-yl)ethyl]β-alanine, and
[2(R)-propyl-4-(piperidin-4-yl)butanoyl-Sar-3(R)-(2-phenethyl)β-alanine.

This invention includes the following abbreviation designations; Sar, sarcosine; Bn, benzyl; NMM, N-methylmorpholine; HOBt, 1-hydroxybenzotriazole; EDC, 1-(3-dimethylaminopropyl)-3-ethylcarbodiimide-hydrochloride; DMF, dimethylformamide; Pib, 4-(4-piperidyl)butanoyl; BOC-Asp(Bn), N-BOC-Asp-β-benzyl ester; pTSA, paratoluenesulfonic acid; DMS, dimethylsulfide; Cbz, carbobenzyloxy; all chiral α-amino acids are of the S-configuration unless otherwise noted.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, and in the prevention of thrombus formation or embolus formation. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, when longer-term treatment may be desirable. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., Amer. J. Physiol., 1987, 252: H, pp 615–621). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically-acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

For intramuscular, intrapertioneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non-toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. Oral administration is presently contemplated as the preferred administration route. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim subsequent to angioplasty. Administration occurs subsequent to angioplasty, and is in an amount sufficient to inhibit platelet aggregation, e.g. an amount which achieves a steady state plasma concentration of between about 0.01-30 $\mu$M preferably between about 1-10 $\mu$M.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention, with or without pharmaceutically acceptable carriers or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amount of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

Generally compounds of the invention can be prepared according to one of the following procedures:

SCHEME I

α-arylalkyl acrylates, such as 1, may be converted to amines by treatment with benzylamine followed by catalytic hydrogenation to remove the benzyl group. The amine addition reaction can be typically run in alkanol solvents, such as MeOH or EtOH, ethers (THF) or halocarbons ($CH_2Cl_2$) at 50°-100° for from 1-24 hours. Coupling of th primary amine (such as 3) with carboxyl-activated forms of dipeptides such as 6; from an N-protected amino-alkanoic acid and glycine, provides diamide such as 7. These amide coupling reactions are carried out under standard conditions and typically employ $CH_2Cl_2$ solutions in which i-butyl chloroformate activates the acid. Other coupling reagents such as DCC, EDC, etc. and other solvents such as DMF, may be used. The N-protected acid may be a linear, cyclic or aromatic compound in which typically CBZ, BOC, or FMOC substitution is used on N. Final deprotection involving basic ester hydrolysis and acidic (HCl gas, $CF_3CO_2H$) N-deprotection provides final products (9)

For the purpose of preparing chiral materials, the α-arylalkyl acrylates may be treated with chiral amines, such as R-(+)-α-methylbenzylamine and the resulting diastereomers are separated by chromatography or crystallization. Typically, these reactions are run either neat or in solution at 30°-130° for 1-18 hours. The resultant chiral amines may be deprotected with loss of the chiral auxilliary, typically by catalytic hydrogenation. The resultant chiral amines may then be coupled to other amino acids or di-peptides using standard coupling techniques.

SCHEME IX

Chiral N-protected aminoalkanoic acids for use as N-terminal components may be prepared from conversion of the appropriate N-protected aminoalkanoic acid (14) to its chiral oxazolidinone analog (45). This conversion typically involves treatment of the requisite acid anhydride with the lithium salt of the chiral oxazolidinone in an ether solvents, such as THF, at −78° to 20°, for from 5 minutes to 3 hours. Alkylation of this chiral oxazolidinne, typically with halides or tosylates, such as methyl iodide, alkyl bromide, benzyl bromide, etc. provides, after basic hydrolysis, the chiral α-substituted acid (such as 47). Coupling of this with amino acids, such as N-methyl glycine, or dipeptides is carried out by carboxylate activation with DCC, i-butyl chloroformate, EDC, and similar reagents, typically in solvents such as DMF or $CH_2Cl_2$ at −25° to 25° C. for from 15 minutes to 18 hours.

SCHEME X

Alkyl esters of 2,3-diaminopropanoic acid (55) are typically coupled to dipeptides, such as N-BOC-Pib-Gly(OH) example (36), via standard coupling methods such as DCC, EDC, i-butylchloroformate, etc. The resulting amino esters (56) may be sulfonylated, acylated, or alkylated on nitrogen. Typically, these reactions would utilize alkyl or aryl sulfonyl halides, acyl halides, isocyanates or anhydrides, and alkyl halides or tosylates and are carried out in solvents such as ethers (THF), halocarbons ($CH_2Cl_2$), polar solvents (DMF) and others (EtOAc) at 0°-100° for from 1-24 hours. Alternatively, the diaminopropanoic acid could be functionalized, i.e. sulfonylated, acylated, etc. prior to coupling to the amino termianl residues.

The compounds of Formula I are prepared according to the reaction schemes set forth below. Compound 1 was prepared according to the methodology set forth in Bull. Soc. Chim. Fr. 1970, 1, 219-230, Fraisse-Jullien, Renee; Frejazille, Claudine, which is incorporated herein by reference.

SCHEME I
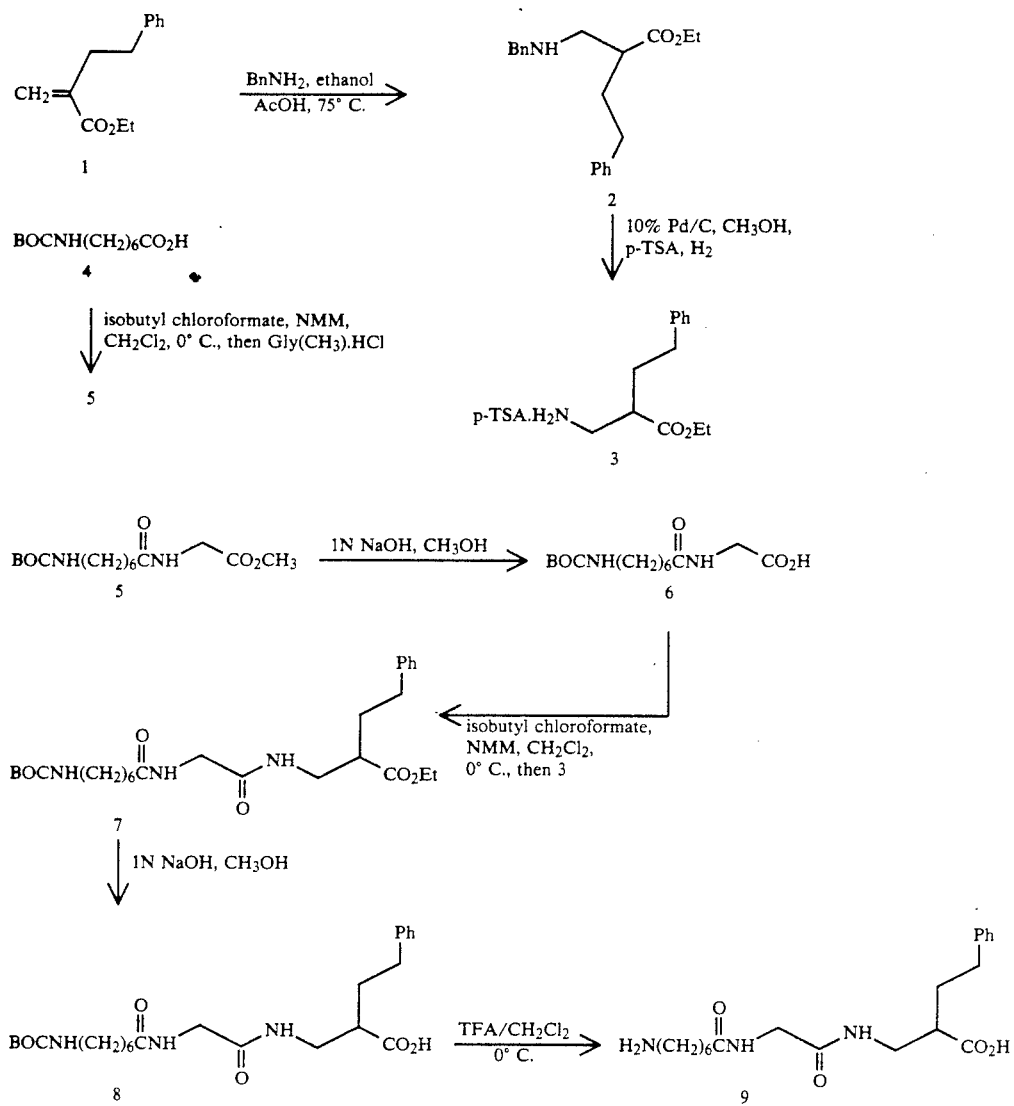
SCHEME II
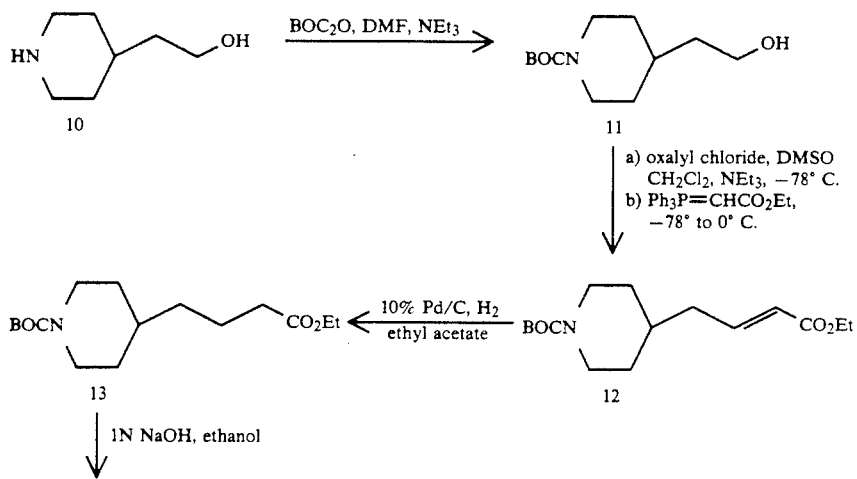

5,264,420
SCHEME II
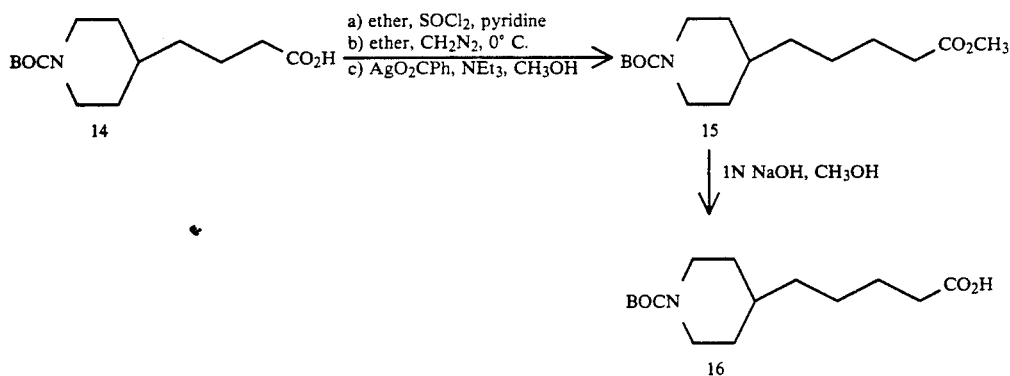
SCHEME III
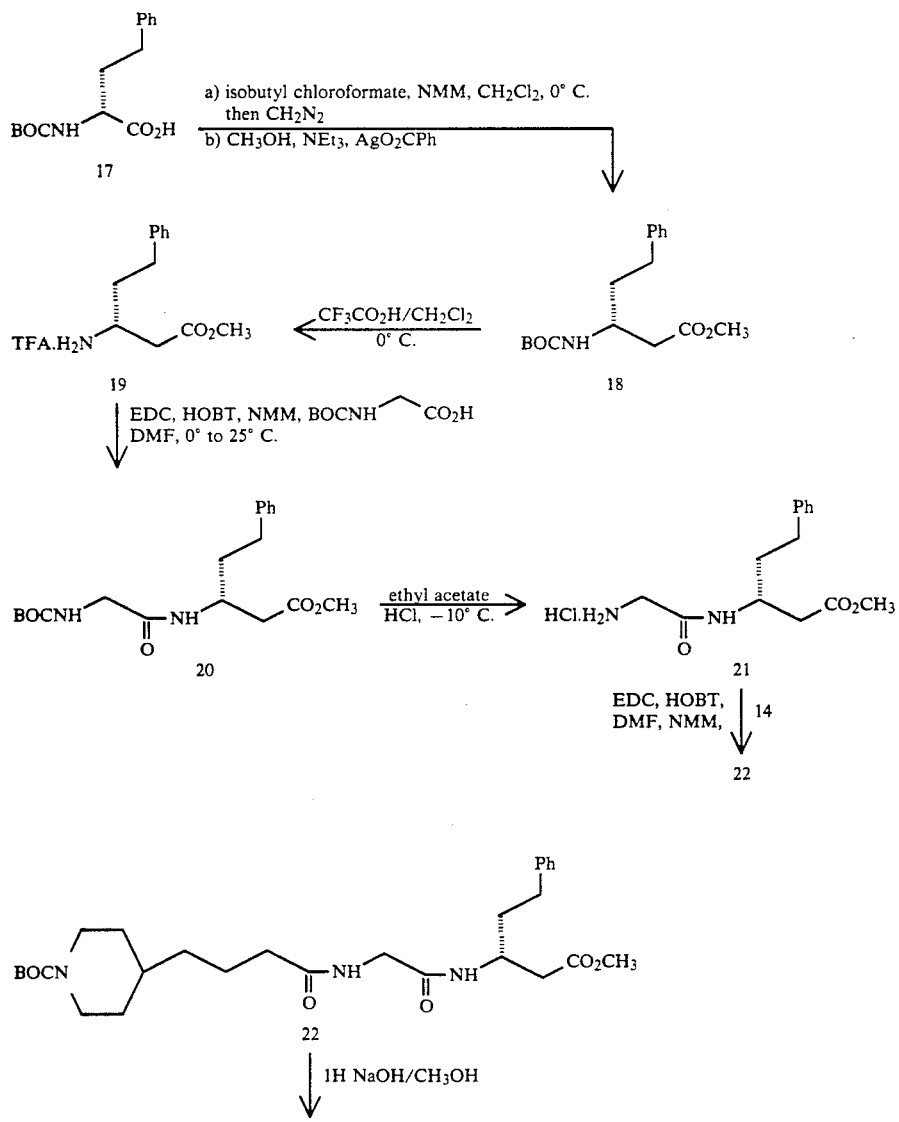

-continued
SCHEME III
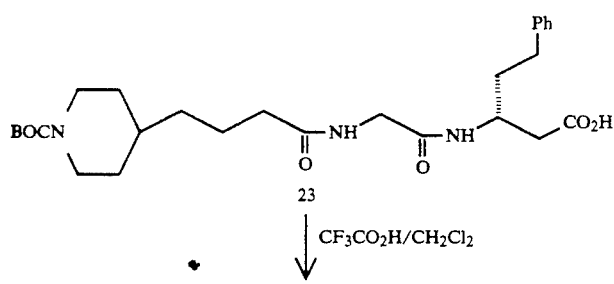
SCHEME IV
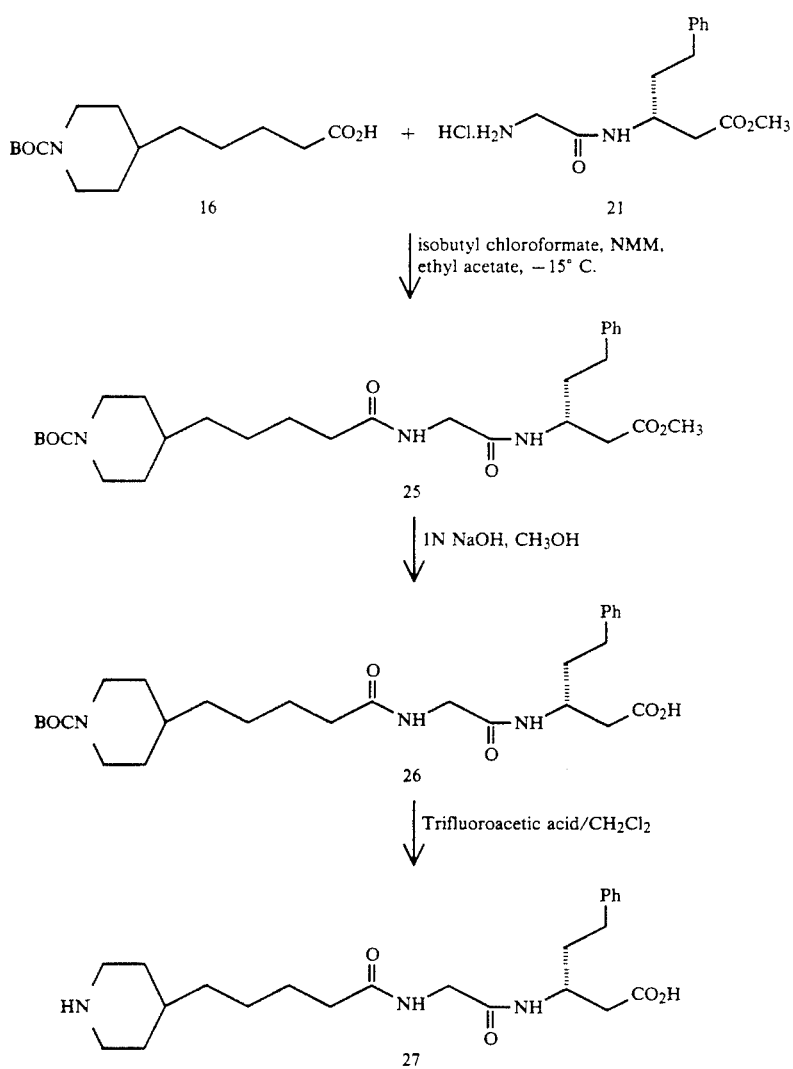

SCHEME V
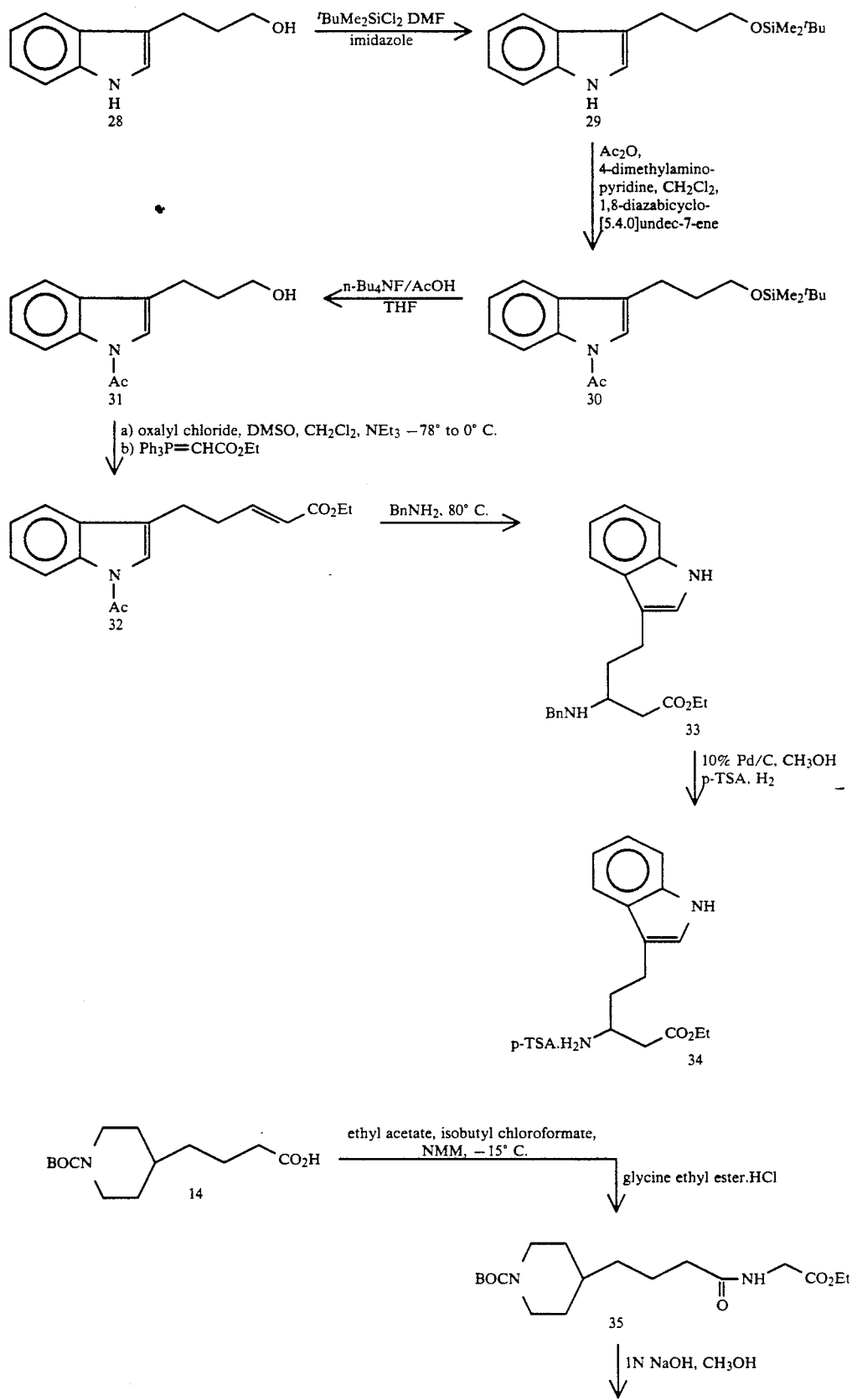

-continued
SCHEME V
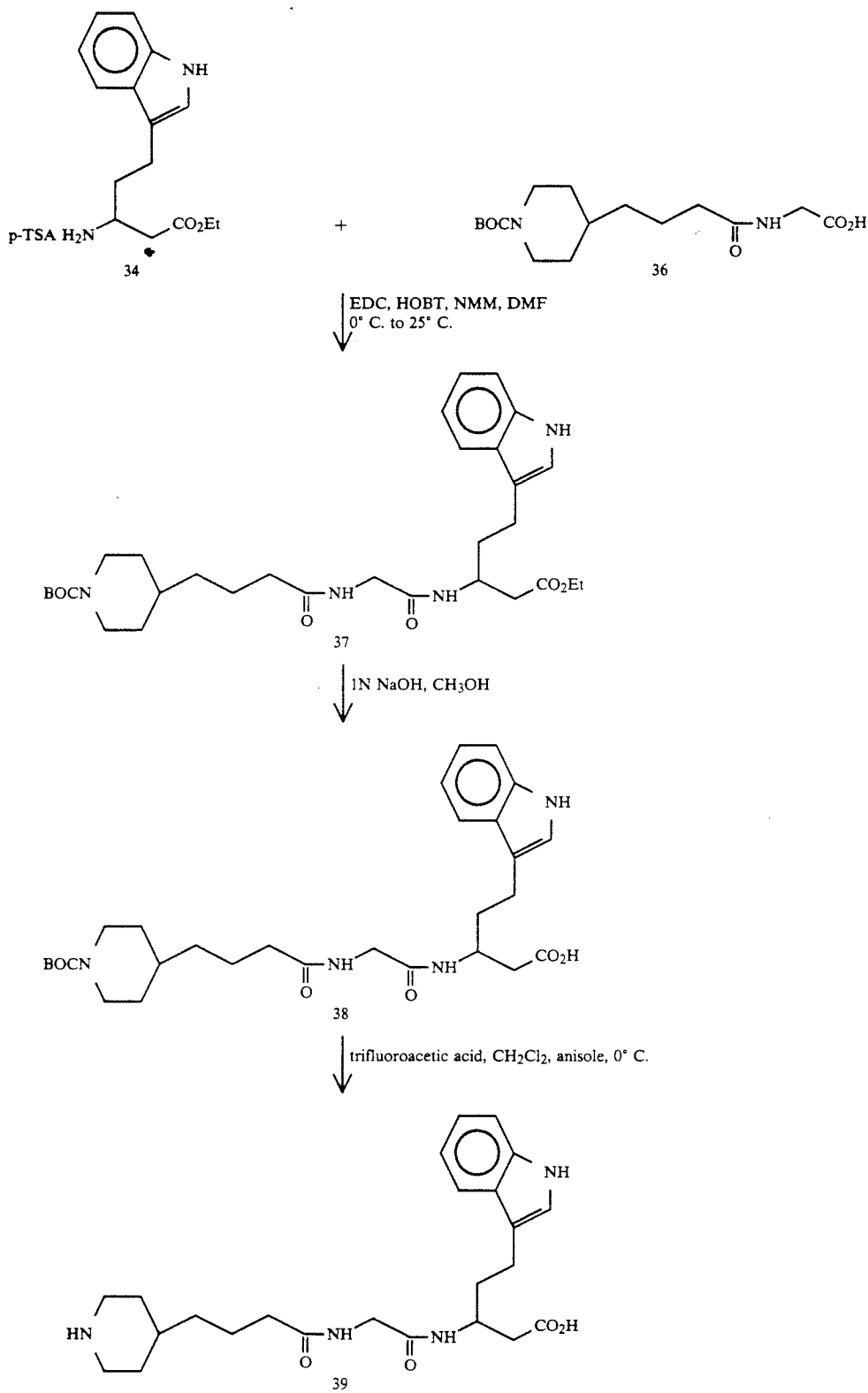

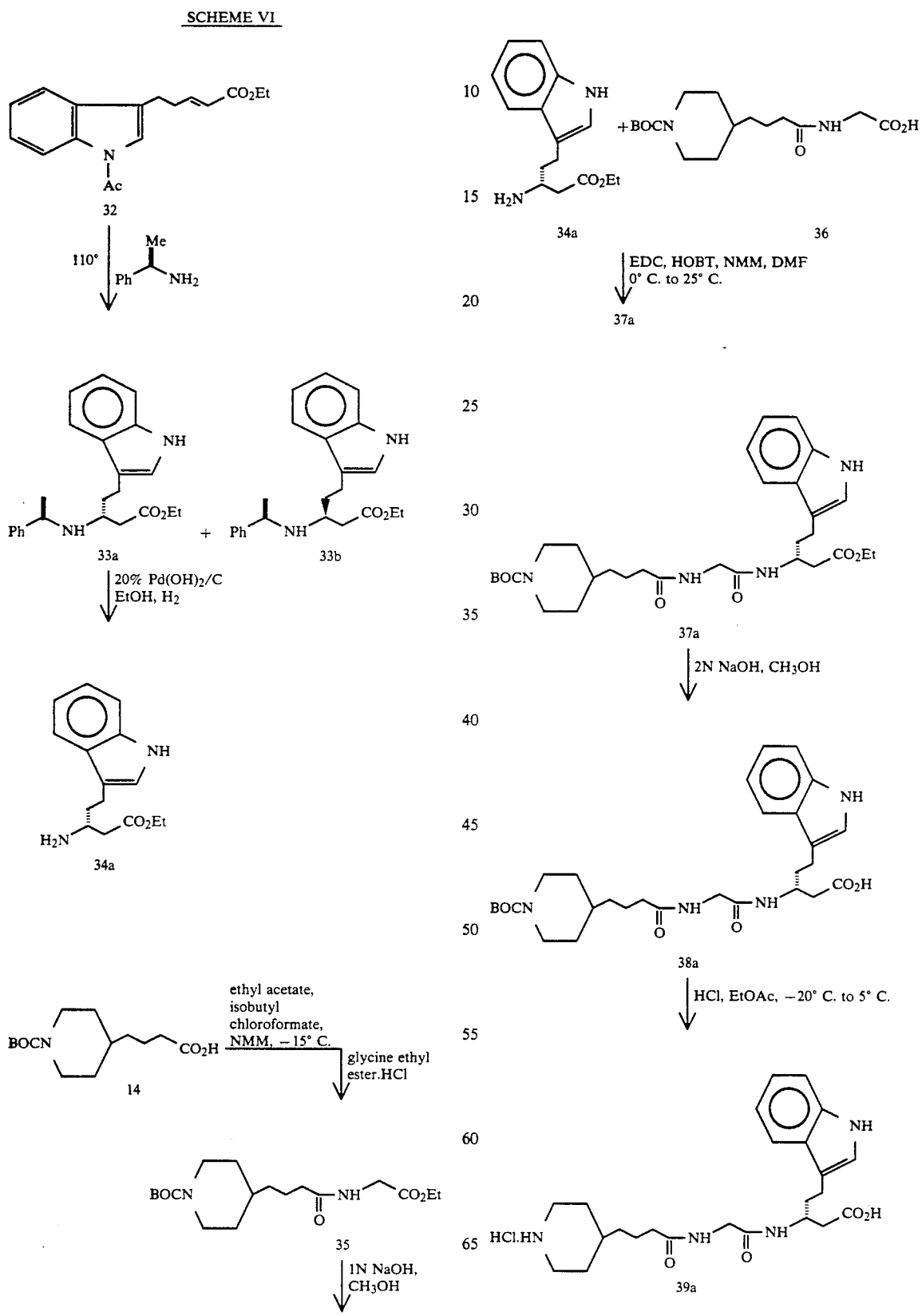

SCHEME VII
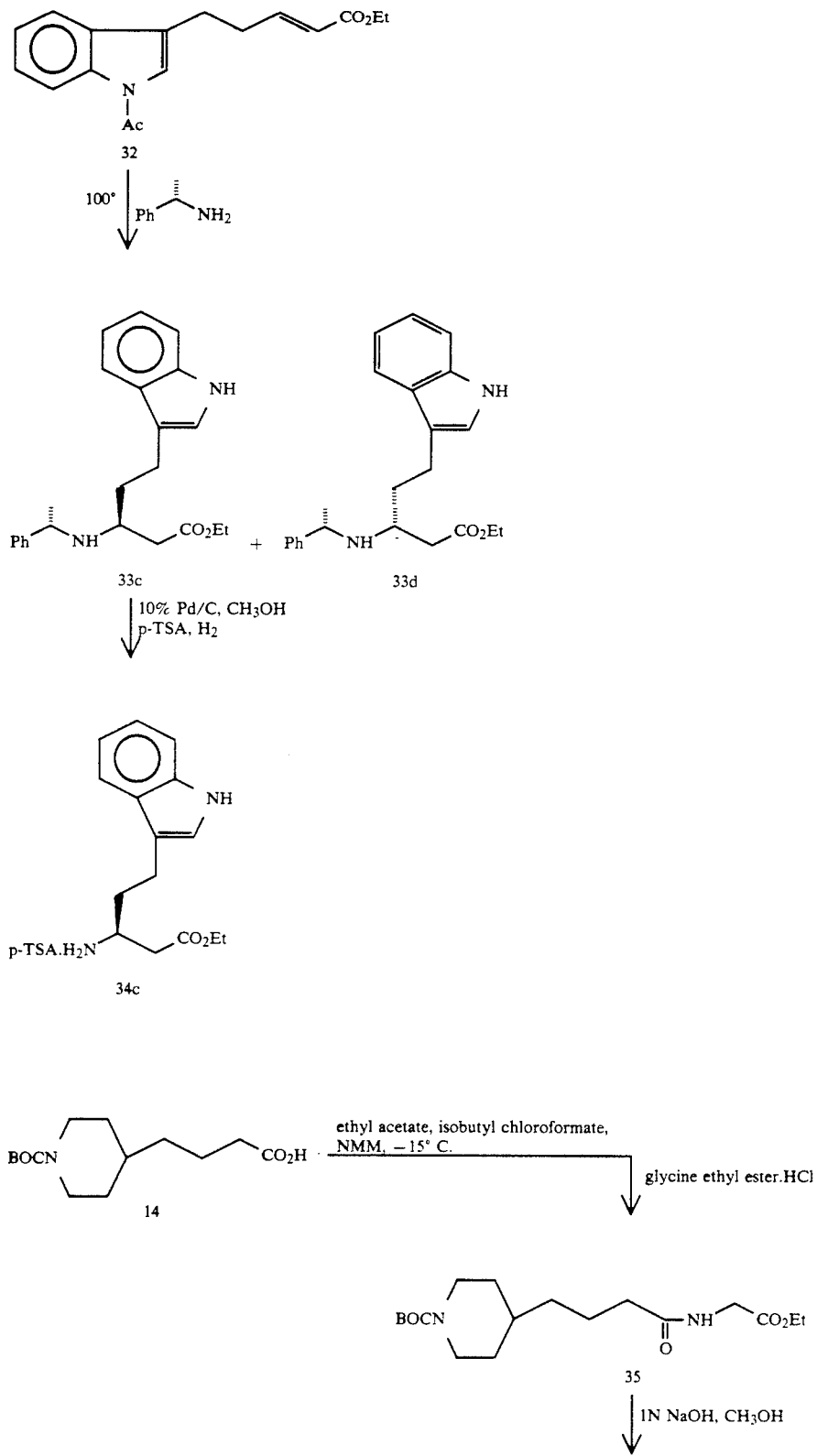

-continued
SCHEME VII
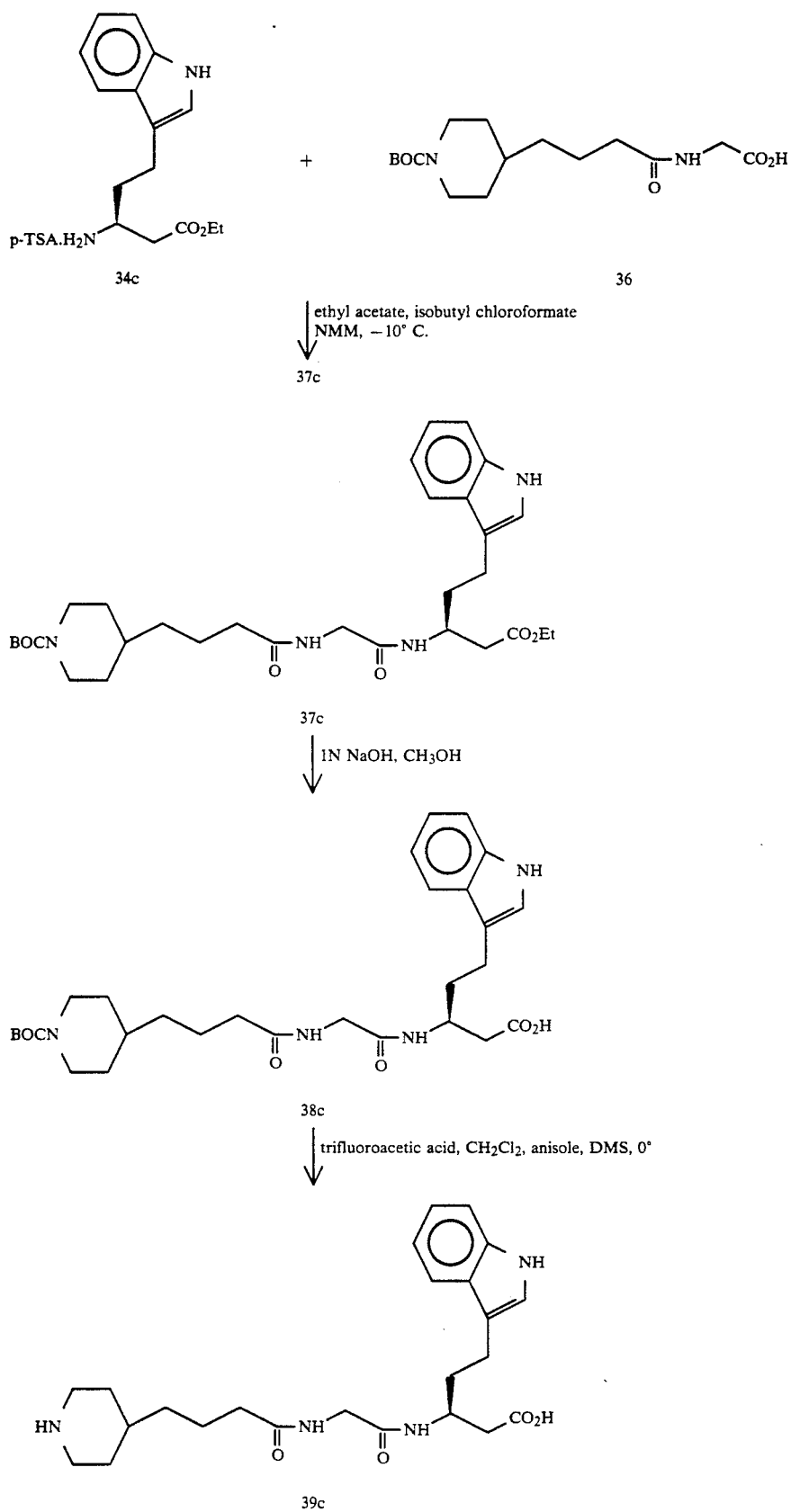

SCHEME VIII
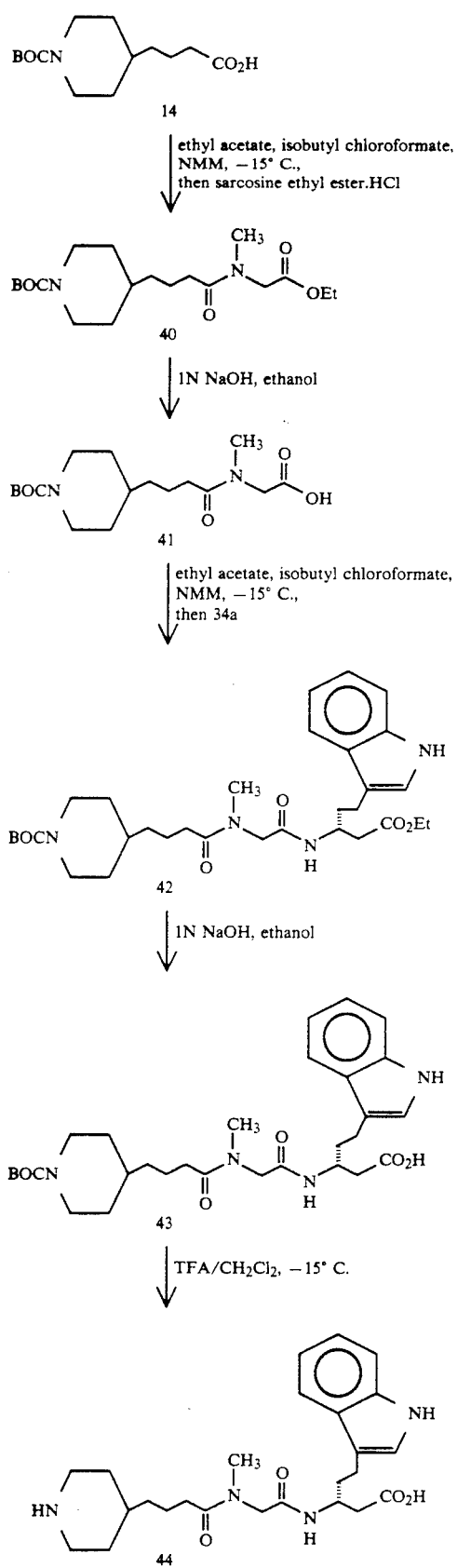
SCHEME IX
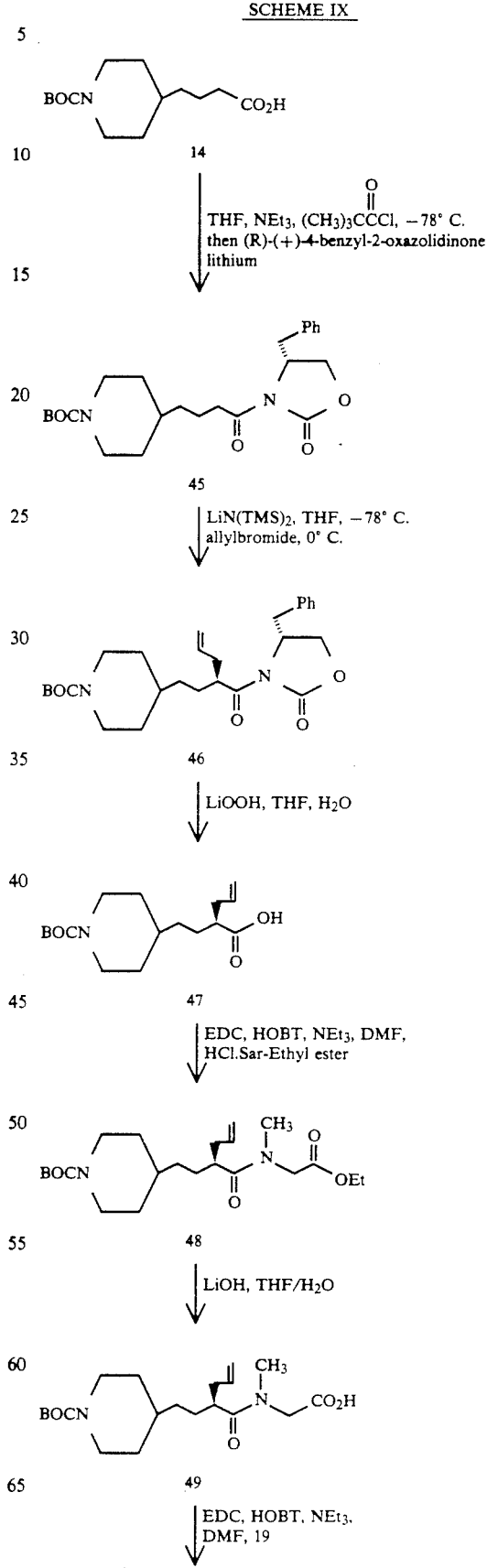

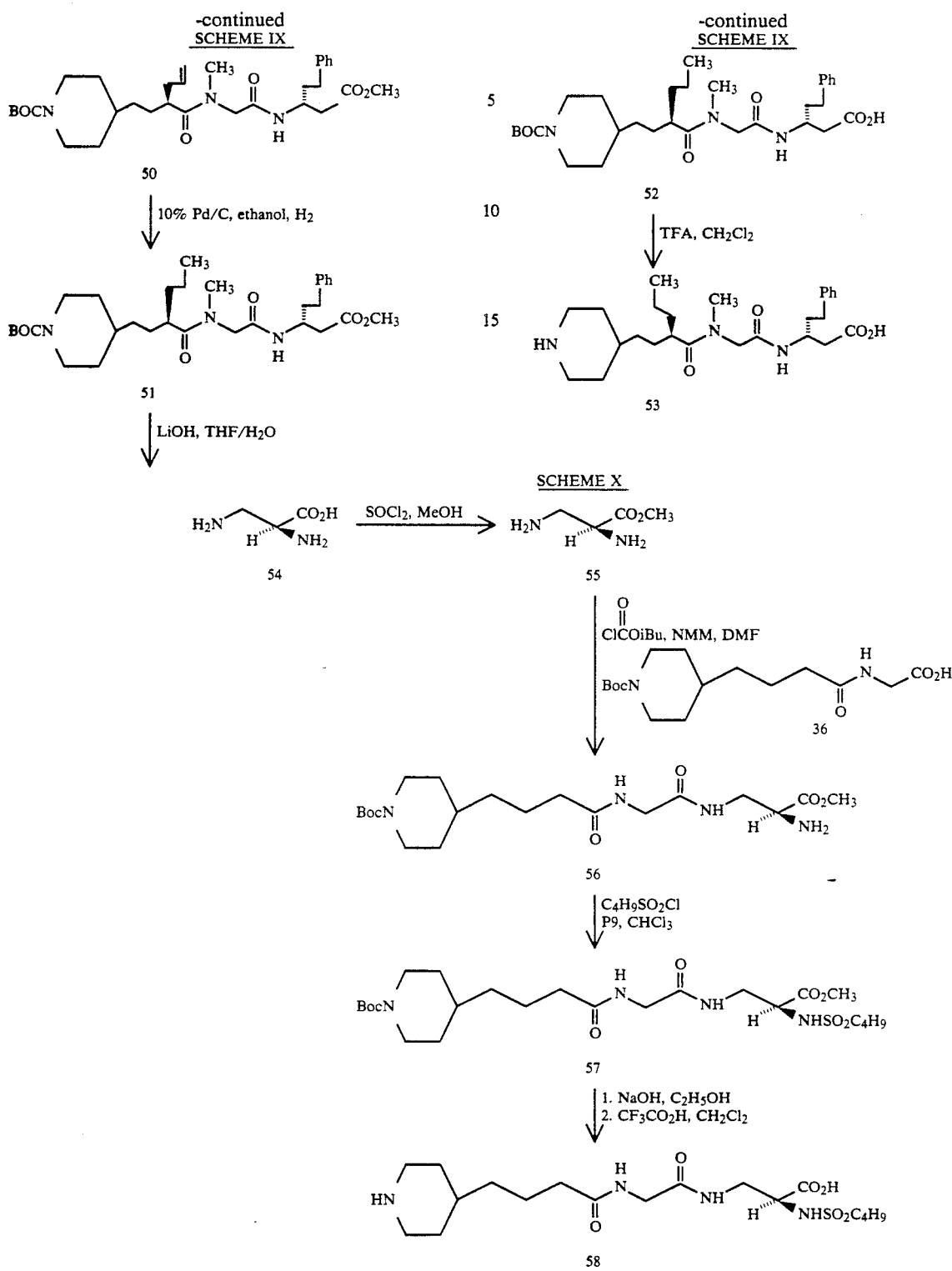

The present invention may be embodied in other specific forms without departing from the spirit or essential attributes thereof. Examples provided are intended to assist in a further understanding of the invention. Particular material employed, species and conditions are intended to be further illustrative of the invention and not limitative of the reasonable scope thereof. All flash column chromatography and TLC analysis were performed on silica gel. All $^1$H NMR spectra were obtained on a Varian 300 MHz instrument unless otherwise indicated in the following examples.

EXAMPLE 1

Preparation of Ethyl [2-(N-benzylaminomethyl)-4-phenyl]butyrate (2)

A mixture of olefin 1 (2.7 g, 13.2 mmol), ethanol (20 mL), benzylamine (1.9 mL, 18.5 mmol), and AcOH (1.4 mL) was stirred for 60 hours at 75° C. The cooled reaction mixture was then diluted with $H_2O$ and acidified to pH=3 with 1N HCl followed by washing with ether (2 times). The aqueous phase was then basified with 1N NaOH to pH=10 followed by extraction with ether (2 times). The ether portion was dried ($MgSO_4$) and concentrated. Flash chromatography (silica, 22% ethyl acetate/hexanes) gave the amine 2 (1.3 g) as a colorless oil.

TLC Rf=0.46 (50% ethyl acetate/hexanes); $^1H$ NMR ($CDCl_3$) $\delta$7.35–7.10 (m, 10H), 4.17 (q, J=7 Hz, 2H), 3.78 (m, 2H), 2.90 (m, H), 2.72 (m, 1H), 2.61 (m, 3H), 1.96 (m, 1H), 1.80 (m, 1H), 1.29 (t, J=7 Hz, 3H).

EXAMPLE 2

Preparation of Ethyl [2-(aminomethyl)-4-phenyl]butyrate p-toluenesulfonic acid salt (3)

A mixture of the benzylamine 2 (1.3 g, 3.3 mmol), 10% Pd/C (200 mg), p-toluenesulfonic acid (0.8 g, 3.3 mmol), and ethanol (50 mL) was stirred under a hydrogen atmosphere (1 atm) at ambient temperature for 3 days. The reaction was purged with argon, the catalyst removed by filtration, and the filtrate concentrated to give the salt 3 (1.6 g) as a colorless oil. TLC Rf=0.42 (10% methanol/$CH_2Cl_2$)

EXAMPLE 3

Preparation of Methyl N-BOC-Aha-Gly (5)

To a stirred solution of acid 4 (2.0 g, 9.9 mmol), NMM (1.3 mL, 11.9 mmol), and $CH_2Cl_2$ (50 mL) at 0° C. was added isobutyl chloroformate (1.6 mL, 11.9 mmol). After 15 minutes, glycine methyl ester.HCl (1.9 g, 15 mmol) was added followed by NMM (19.8 mmol, 2.2 mL). After 2 hours the reaction mixture was diluted with ethyl acetate and then washed with 50% brine, dried ($MgSO_4$), and concentrated. Flash chromatography (silica, 25% ethyl acetate/hexanes to ethyl acetate) furnished the dipeptide 5 (2.6 g) as a white solid. TLC Rf=0.61 (ethyl acetate).

EXAMPLE 4

Preparation of N-BOC-Aha-Gly (6)

A solution of ester 5 (2.6 g, 8.2 mmol), 1N NaOH (12.3 mL, 12.3 mmol), and $CH_3OH$ (130 mL) was stirred at ambient temperature for 20 hours. The reaction mixture was concentrated to remove the $CH_3OH$ then diluted with $H_2O$ and acidified with 5% $KHSO_4$. The aqueous phase was then extracted with ethyl acetate and the ethyl acetate portion concentrated to furnish the carboxylic acid 6 (2.1 g) as a colorless oil.

TLC Rf=0.70 (9:1:1 $CH_2Cl_2$/AcOH/$CH_3OH$).

EXAMPLE 5

Preparation of N-BOC-Aha-Gly-2-(2-phenethyl)$\beta$-alanine ethyl ester (7)

To a stirred solution of carboxylic acid 6 (0.41 g, 1.32 mmol), NMM (0.18 mL, 1.63 mmol), and $CH_2Cl_2$ (5 mL) at 0° C. was added isobutyl chloroformate (0.21 mL, 1.63 mmol). After 20 minutes the amine salt 3 (0.20 g, 0.54 mmol) was added followed by NMM (0.36 mL, 3.2 mmol). After 20 hours the reaction was diluted with ethyl acetate then washed with $H_2O$ and brine, dried ($MgSO_4$), and concentrated. Flash chromatography (silica, 65% to 85% ethyl acetate/hexanes) gave the tripeptide 7 (90 mg) as a colorless oil.

TLC Rf=0.42 (ethyl acetate). $^1H$ NMR ($CDCl_3$) $\delta$7.30–7.15 (m, 5H), 6.88 (t, J=6 Hz, 1H), 6.69 (t, J=5 Hz, 1H), 4.68 (bs, 1H), 4.14 (q, J=7 Hz, 2H), 3.88 (d, J=4 Hz, 2H), 3.46 (m, 2H), 3.08 (m, 2H), 2.62 (m, 3H), 2.23 (t, J=7Hz, 2H), 1.96 (m, 1H), 1.80 (m, 1H), 1.63 (m, 2H), 1.43 (S, 9H), 1.28 (t, J=7 Hz, 3H).

EXAMPLE 6

Preparation of N-BOC-Aha-Gly-2-(2-phenethyl)$\beta$-alanine) (8)

A solution of ester 7 (90 mg, 0.18 mmol), 1N NaOH (2.0 mL, 2.0 mmol), and $CH_3OH$ (4 mL) was stirred at ambient temperature for 1.5 hours. The reaction mixture was then acidified with 5% $KHSO_4$ followed by extraction with ethyl acetate (3 times). The extracts were then combined, dried ($MgSO_4$), and concentrated to give the carboxylic acid 8 (70 mg) as a colorless oil.

TLC Rf=0.84 (9.5:2.5:2.5 ethanol/$NH_4OH$/$H_2O$); $^1H$ NMR ($CD_3OD$) $\delta$7.21 (m, 5H), 4.80 (S, 2H), 3.42 (m, 2H), 2.99 (t, J=7 Hz, 2H), 2.63 (m, 3H), 2.24 (t, J=7 Hz, 2H), 1.82 (m, 2H), 1.61 (m, 2H), 1.50–1.30 (m, 6H), 1.43 (S, 9H).

EXAMPLE 7

Preparation of Aha-Gly-2-(2-phenethyl)$\beta$-alanine (9)

To a stirred solution of 8 (70 mg, 0.15 mmol) in $CH_2Cl_2$ (2.0 mL) at 0° C. was added trifluoroacetic acid (TFA; 200 $\mu$l) followed by removal of the cooling bath. After 1.5 hours the solvent was evaporated and the resulting yellow oil subjected to flash chromatography (silica, 94:3:3 ethanol/$H_2O$/$NH_4OH$) to afford the amino acid 9 (30 mg) as a white powder.

TLC Rf=0.22 (9.5:2.5:2.5 ethanol/$H_2O$/$NH_4OH$); $^1H$ NMR ($D_2O$) $\delta$7.32 (m, 5H), 3.85 (s, 2H), 3.33 (m, 2H), 2.82 (t, J=7 Hz, 2H), 2.61 (m, 2H), 2.45 (m, 1H), 2.30 (t, J=7 Hz, 2H), 1.77 (m, 2H), 1.60 (m, 4H), 1.33 (m, 4H).

EXAMPLE 8

Preparation of N-BOC-4-piperidineethanol (11)

To a stirred solution of 4-piperidine-ethanol 10 (18.7 g, 0.14 mol) and DMF (200 mL) at 0° C. was added N-tert-butoxoxycarbonyl anhydride (31 g, 0.14 mol). After 1.0 hour the cooling bath was removed and the reaction mixture stirred for 20 hours. The reaction mixture was diluted with ether and then washed with $H_2O$ (2 times) and brine, dried ($MgSO_4$), and concentrated to furnish 11 (26 g) as a colorless oil.

TLC Rf=0.25 (40% ethyl acetate/hexanes); $^1H$ NMR ($CDCl_3$) $\delta$4.09 (bs, 2H), 3.72 (t, J=7 Hz, 2H), 2.70 (m, 2H), 1.75–1.10 (m, 7H), 1.46 (s, 9H).

EXAMPLE 9

Preparation of Ethyl 4-(N-BOC-4-piperidyl)trans-crotonate (12)

To a stirred solution of oxalyl chloride (0.43 mL, 5.0 mmol) in $CH_2Cl_2$ (20 mL) at $-78°$ C. was added DMSO (0.52 ml, 7.0 mmol) dropwise. After gas evolution subsided (~5 minutes) the alcohol 11 (0.8 g, 3.5 mmol) in $CH_2Cl_2$ (20 mL) was added in a stream. After 20 minutes triethylamine (1.7 mL, 12 mmol) was added dropwise and then the cooling bath removed. After 20 minutes (carbethoxymethylene) triphenylphosphorane (1.4 g, 4.0 mmol) was added. After 2.0 hours the reaction mixture was diluted with petroleum ether and then washed sequentially with $H_2O$, 5% $KHSO_4$, and brine, dried ($MgSO_4$), and concentrated. Flash chromatography (silica, 15% ethyl acetate/hexanes) gave the ester 12 (0.57 g) as a colorless oil.

TLC Rf=0.79 (50% ethyl acetate/hexanes); $^1H$ NMR ($CDCl_3$) δ6.91 (dt, J=16 and 7 Hz, 1H), 5.81 (bd, J=17 Hz, 1H), 4.18 (q, J=7 Hz, 2H), 4.08 (m, 2H), 2.67 (m, 2H), 2.14 (t, J=7 Hz, 2H), 1.70–1.05 (m, 5H), 1.44 (S,9H), 1.28 (t, J=7H, 3H).

EXAMPLE 10

Preparation of Ethyl 4-(N-BOC-4-piperidyl) butyrate (13)

The olefin 12 (26 g, 87 mmol) in ethyl acetate (500 mL) was hydrogenated, at ambient temperature, under a hydrogen atmosphere (1 atm) in the presence of 10% Pd/C (5.0 g) overnight. The reaction mixture was then purged with argon followed by filtration through a celite pad. Concentration of the filtrate followed by flash chromatography (silica, 10% ethyl acetate/hexanes) gave the ester 13 (24 g) as a crystalline solid.

TLC Rf=0.52 (20% ethyl acetate/hexanes); $^1H$ NMR ($CDCl_3$) δ4.16 (q, J=7 Hz, 2H), 4.10 (m, 2H), 2.69 (m, 2H), 2.31 (t, J=7 Hz, 2H), 1.68 (m, 4H), 1.38 (s, 9H), 1.40 (m, 1H), 1.11 (m, 2H).

EXAMPLE 11

Preparation of 4-(N-BOC-4-piperidyl)butanoic acid (14)

A solution of ester 13 (19 g, 63 mmol), ethanol (300 mL) and 1N NaOH (100 mL, 100 mmol) was stirred at ambient temperature for 2.5 hours followed by concentration. The residue was diluted with 5% $KHSO_4$ and ethyl acetate and transferred to a separatory funnel. The phases were shaken then separated and the organic portion was washed with brine, dried ($MgSO_4$), and concentrated to give the acid 14 (18 g) as a colorless oil that crystallized upon standing.

TLC Rf=0.68 (ethyl acetate).

EXAMPLE 12

Preparation of Methyl 5-(4-piperidyl)pentanoate (15)

To a stirred solution of carboxylic acid 14 (600 mg, 2.2 mmol), ether (4.0 mL), and pyridine (2 drops) at ambient temperature was added thionyl chloride in one portion to effect an exotherm. After 25 minutes the ether, pyridine, and thionyl chloride were evaporated. The intermediate acid chloride was dissolved in ether (5 mL), cooled to 0° C., then treated with an ethereal solution of diazomethane (15 mL, ~10 mmol). After 2.0 hours the excess diazomethane was removed by purging with argon. Evaporation in situ gave a solid that was dissolved in $CH_3OH$ (10 mL) then treated sequentially with $NEt_3$ (0.5 mL) and silver benzoate (20 mg). After 15 minutes the black reaction mixture was concentrated and the residue subjected to flash chromatography (silica, 10% ethyl acetate/hexanes) to give 15 (300 mg) as an oil.

TLC Rf=0.73 (30% ethyl acetate/hexanes); $^1H$ NMR ($CDCl_3$) δ4.09 (m, 2H), 3.69 (s, 3H), 2.68 (m, 2H), 2.33 (t, J=7 Hz, 2H), 1.80–1.00 (m, 11H), 1.47 (s, 9H).

EXAMPLE 13

Preparation of N-BOC-5-(4-piperidyl)pentanoic acid (16)

A mixture of ester 15 (200 mg, 0.7 mmol), in NaOH (1.0 mL, 1.0 mmol), and $CH_3OH$ (4.0 mL) was stirred at ambient temperature for 20 hours. The reaction mixture was then diluted sequentially with 5% $KHSO_4$ and ethyl acetate. The ethyl acetate portion was washed with brine, dried ($MgSO_4$), and concentrated to give the carboxylic acid 16 (190 mg) as a colorless oil.

TLC Rf=0.70 (ethyl acetate).

EXAMPLE 14

Preparation of N-BOC-3(R)-(2-phenethyl)β-alanine methyl ester (18)

To a stirring solution of N-BOC-D-homophenylalanine 17 (15 g, 53.7 mmol), NMM (7.1 mL, 64.4 mmol) and $CH_2Cl_2$ (270 mL) at 0° C. was added a isobutyl chloroformate (8.4 mL, 64.4 mmol). After 15 minutes an ethereal solution of diazomethane (120 mL, 75 mmol) was added in portions. The cooling bath was then removed and the reaction stirred for 1.5 hours. The reaction mixture was then purged with argon for 15 minutes to remove excess diazomethane. Dilution with ethyl acetate followed by washing with sat. $NaHCO_3$, $H_2O$ and brine, drying ($MgSO_4$) and concentrating to give the crude diazoketone. The diazoketone was dissolved in $CH_3OH$ (300 mL) and then treated sequentially with $AgO_2CPh$ (4.3 g, 19 mmol) and $NEt_3$ (24 mL, 172 mmol). After 20 hours the reaction was concentrated then subjected to flash chromatography (silica, 10% ethyl acetate/hexanes) to yield the methyl ester 18 (5.0 g) as a white solid. TLC Rf=0.38 (20% ethyl acetate/hexanes).

EXAMPLE 15

Preparation of 3(R)-(2-phenethyl)β-alanine methyl ester-TFA salt (19)

A mixture of 18 (3.2 g, 10.9 mmol), trifluoroacetic acid (55 mL), and $CH_2Cl_2$ (55 mL) was stirred at 0° C. for 1 hour. Concentration followed by azeotropic removal of residual trifluoroacetic acid with toluene (2 times) gave the TFA.salt 19 (4.3 g) as a yellow oil.

TLC Rf=0.40 (9:1:1 $CH_2Cl_2/CH_3OH/AcOH$).

EXAMPLE 16

Preparation of BOC-Gly-3(R)-(2-phenethyl)β-alanine methyl ester (20)

To a stirring solution of BOC-Gly (2.1 g, 12.0 mmol), amine 19 (3.3 g, 10.9 mmol), HOBT (2.2 g, 16.3 mmol), NMM (3.9 mL, 36 mmol), and dry DMF (55 mL) at 0° C. was added EDC (2.9 g, 15.2 mmol) followed by removal of the cooling bath. After 20 hours, the reaction mixture was diluted with ethyl acetate and then washed sequentially with $H_2O$, sat. $NaHCO_3$, 5% $KHSO_4$, $H_2O$ and brine, dried ($MgSO_4$), and concentrated. Flash chromatography (silica, 35% ethyl acetate/hexanes) gave the dipeptide 20 (2.1 g) as a colorless oil.

TLC Rf=0.37 (50% ethyl acetate/hexanes).

EXAMPLE 17

Preparation of Gly-3(R)-(2-phenethyl)β-alanine methyl ester.HCl salt (21)

HCl gas was bubbled through a solution of dipeptide 20 (2.0 g, 5.7 mmol) in ethyl acetate (200 mL) at −10° C. for 15 minutes. The reaction mixture was then purged with argon for 15 minutes to remove the excess HCl. Concentration gave a white solid that was triturated with ether to give the HCl.salt 21 (1.7 g).

$^1$H NMR (CDCl$_3$) δ8.31 (bs, 1H), 8.10 (bs, 3H), 7.15 (m, 5H), 4.25 (bs, 1H), 4.04 (m, 2H), 3.57 (s, 3H), 2.65 (m, 1H), 2.50 (m, 4H), 1.78 (m, 2H).

EXAMPLE 18

Preparation of N-BOC-Pib-Gly-3(R)-(2-phenethyl)β-alanine methyl ester (22)

To a stirred solution of the carboxylic acid 14 (205 mg, 0.76 mmol), 21 (200 mg, 0.67 mmol) HOBT (140 mg, 1.0 mmol), NMM (0.25 mL, 2.3 mmol), and DMF (3.5 mL) at 0° C. was added EDC (185 mg, 0.97 mmol) followed by removal of the cooling bath. After 20 hours the reaction mixture was diluted with ethyl acetate and then washed with H$_2$O (2 times) and brine, dried (MgSO$_4$), and concentrated. Flash chromatography (silica, 85% ethyl acetate/hexanes) gave 22 (150 mg) as a colorless oil.

TLC Rf=0.99 (80% ethyl acetate/hexanes).

EXAMPLE 19

Preparation of N-BOC-Pib-Gly-3(R)-(2-phenethyl)β-alanine (23)

A mixture of the methyl ester 22 (150 mg, 0.30 mmol), CH$_3$OH (3 mL), and 1N NaOH (1.0 mL, 1.0 mmol) was stirred at ambient temperature for 1.5 hours. The reaction mixture was sequentially diluted with 5% KHSO$_4$ and ethyl acetate. The ethyl acetate portion was washed with brine, dried (MgSO$_4$), and concentrated to give the carboxylic acid 23 (150 mg) as a colorless oil.

TLC Rf=0.41 (9:0.5:0.5 CH$_2$Cl$_2$/CH$_3$OH/AcOH); $^1$H NMR (CDCl$_3$) δ7.40–7.07 (m, 6H), 6.71 (t, J=4 Hz, 1H), 4.30 (m, 1H), 4.05 (m, 2H), 3.90 (m, 2H), 3.66 (s, 3H), 2.65 (m, 3H), 2.55 (d, J=6 Hz, 2H), 2.23 (t, J=7 Hz, 2H), 1.88 (m, 1H), 1.65 (m, 4H), 1.46 (s, 9H), 1.30 (m, 1H), 1.06 (m, 2H).

EXAMPLE 20

Preparation of Pib-Gly-3(R)-(2-phenethyl)β-alanine (24)

A solution of 23 (150 mg, 0.30 mmol), trifluoroacetic acid (1.0 mL) and CH$_2$Cl$_2$ (1.0 mL) was stirred at ambient temperature for 45 minutes followed by evaporation. Flash chromatography (silica 10:0.8:0.8 ethanol/H$_2$O/NH$_4$OH) gave the amino acid 24 (35 mg) as a white solid.

TLC Rf=0.17 (10:1:1 ethanol/NH$_4$OH/H$_2$O; $^1$H NMR (CDCl$_3$) δ7.40 (m, 5H), 4.42 (m, 1H), 4.10 (d,J=17 Hz, 1H), 4.01 (d, J=17 Hz, 1H), 3.15 (m, 2H), 2.86 (t, J=8 .Hz, 2H), 2.61 (m, 2H), 2.52 (t, J=7 Hz, 2H), 2.15–1.55 (m, 9H).

EXAMPLE 21

Preparation of N-BOC-(5-(4-piperidyl)pentanoyl)-Gly-3(R)-(2-phenethyl)β-alanine methyl ester (25)

To a stirred solution of the carboxylic acid 16 (100 mg, 0.35 mmol), NMM (40 μL, 0.35 mmol), and ethyl acetate at −15° C. was added isobutyl chloroformate (45 μL, 0.35 mmol). After 15 minutes the amine.HCl 21 (100 mg, 0.34 mmol) and NMM (40 μL, 0.35 mmol) was added and stirring continued for an additional 1.5 hour. The reaction mixture was washed with H$_2$O, sat. NaHCO$_3$, 5% KHSO$_4$, and brine, dried (MgSO$_4$), and concentrated. Flash chromatography (silica, 70% ethyl acetate/hexanes) gave 25 (110 mg) as an oil.

TLC Rf=0.26 (ethyl acetate).

EXAMPLE 22

Preparation of N-BOC-(5-(4-piperidyl)pentanoyl)-Gly-3(R)-(2-phenethyl)β-alanine (26)

A mixture of ester 25 (110 mg, 0.21 mmol), 1N NaOH (0.4 mL, 0.42 mmol), and CH$_3$OH (5 mL) at ambient temperature was stirred for 20 hours. The reaction mixture was concentrated to dryness, then dissolved in H$_2$O and acidified with 5% KHSO$_4$ (pH ~3.0), followed extraction with ethyl acetate. The ethyl acetate portion was then washed with brine, dried (MgSO$_4$), and concentrated to give the carboxylic acid 26 (107 mg) as a colorless oil.

The Rf=0.40 (9:0.5:0.5 CH$_2$Cl$_2$/CH$_3$OH/AcOH); $^1$H NMR (CD$_3$OD) δ7.20 (m, 5H), 4.22 (m, 1H), 4.01 (m, 2H), 3.80 (m, 2H), 2.65 (m, 3H), 2.50 (d, J=6 Hz, 2H), 2.26 (t, J=7 Hz, 2H), 1.84 (m, 2H), 1.63 (m, 4H), 1.37 (m, 2H), 1.27 (m, 2H) 1.42 (s, 9H), 1.00 (m, 2H).

EXAMPLE 23

Preparation of 5-[(4-piperidyl)pentanoyl)]-Gly-3(R)-(2-phenethyl)β-alanine (27)

A solution of 26 (100 mg, 0.20 mmol), trifluoroacetic acid (4.5 mL), and CH$_2$Cl$_2$ (4.5 mL) was stirred at 0° C. for 1.0 hour. The reaction mixture was then concentrated. Flash chromatography (silica, 10:1:1 ethanol NH$_4$OH/H$_2$O) gave the amino acid 27 (30 mg) as a white solid.

$^1$H NMR (D$_2$O) δ7.20 (m, 5H), 4.17 (m, 1H), 4.81 (m, 2H), 3.28 (m, 2H), 2.86 (m, 2H), 2.63 (t, J=7 Hz, 2H), 2.36 (m, 2H), 2.29 (t, J=7 Hz, 2H), 1.90–1.28 (m, 11).

EXAMPLE 24

Preparation of 3-(Indol-3-yl)propanol-tert-butyldimethylsilyl ether (29)

To a stirring solution of 3-indolepropanol 28 (15 g, 86 mmol), DMF (200 mL), and imidazole (12.8 g, 0.19 mol) at 0° C. was added tert-butyldimethylsilyl chloride (14.2 g, 95 mmol) followed by removal of the cooling bath. After 20 hours the reaction mixture was diluted with ether and then washed with H$_2$O (2 times) and brine, dried (MgSO$_4$), and concentrated to yield the silyl ether 29 (29 g) as an amber oil.

TLC Rf=0.54 (20% ethyl acetate/hexanes); $^1$H NMR (CDCl$_3$) δ8.07 (bs, 1H), 7.77 (d, J=7 Hz, 1H), 7.49 (d, J=7 Hz, 1H), 7.33 (t, J=7 Hz, 1H), 7.26 (t, J=7 Hz, 1H), 7.12 (s, 1H), 3.84 (t, J=6 Hz, 2H), 2.95 (t, J=7

Hz, 2H), 2.08 (m, 2H), 1.08 (s, 9H), 0.25 (s, 3H), 0.22 (s, 3H).

EXAMPLE 25

Preparation of
N-Acetyl-3-(indol-3-yl)propanol-tert-butyldimethylsilyl ether (30)

A solution of the indole 29 (29 g, 86 mmol), CH$_2$Cl$_2$ (450 mL), 1,8-diazobicyclo[5.4.0]undec-7-ene (38 mL, 0.26 mol), 4-dimethylaminopyridine (1.0 g, 8.5 mmol), and acetic anhydride (32 mL, 0.34 mol) was stirred for 1 week at ambient temperature. The reaction mixture was concentrated and then diluted with ether. The ether was then washed with H$_2$O, 5% KHSO$_4$ and brine, dried (MgSO$_4$), and concentrated. Flash chromatography (silica, 5% ethyl acetate/hexanes) gave the acylated product 30 (27 g) as a yellow oil. TLC Rf=0.56 (20% ethyl acetate/hexanes).

EXAMPLE 26

Preparation of N-Acetyl-3-(indol-3-yl)propanol (31)

To a stirred solution of the silyl ether 30 (27 g, 81 mmol) in THF (270 mL) at ambient temperature was added a premixed solution of n-Bu$_4$NF (1M in THF: 244 mL, 0.24 mol) and AcOH (14 mL, 0.24 mmol) (1:1). After 20 hours the reaction mixture was diluted with ether and then washed with H$_2$O (2 times) and brine, dried (MgSO$_4$), and concentrated to give the alcohol 31 (19 g) as a yellow crystalline solid.

TLC Rf=0.35 (60% ethyl acetate/hexanes); $^1$H NMR (CDCl$_3$) δ8.42 (m, 1H), 7.55 (d, J=7 Hz, 1H), 7.36 (t, J=7 Hz, 1H), 7.29 (t, J=7 Hz, 1H), 7.27 (7d, J=7 Hz, 1H), 7.22 (s, 1H), 3.76 (t, J=7 Hz, 2H), 2.82 (t, J=7 Hz, 2H), 2.61 (s, 3H), 2.00 (m, 2H).

EXAMPLE 27

Preparation of 5-(N-Acetylindol-3-yl)pent-2-enoic acid ethyl ester (32)

To a stirring solution of oxalyl chloride (11.4 mL, 0.13 mol) in CH$_2$Cl$_2$ (440 mL) at −78° C. was added dry DMSO (2.4 mL, 0.17 mol) dropwise. After 5 minutes, gas evolution ceased and the alcohol 31 (19 g, 87 mmol) in CH$_2$Cl$_2$ (40 mL) was added. After 30 minutes, NEt$_3$ (73 mL, 0.52 mol) was added to effect a thick slurry. The cooling bath was removed and the reaction stirred for an additional 15 minutes before adding (carbethoxymethylene)triphenyl phosphorane (33.5 g, 96 mmol). After 2.0 hours, the reaction mixture was diluted with ether and then washed with H$_2$O (2 times), 5% KHSO$_4$ and brine, dried (MgSO$_4$), and concentrated. Flash chromatography (20% ethyl acetate/hexanes) gave the olefin 32 (14 g) as a white solid.

TLC Rf=0.54 (60% ethyl acetate/hexanes); $^1$H NMR (CDCl$_3$) 8.42 (bd, 1H), 7.50 (d, J=7 Hz, 1H), 7.34 (t, J=7 Hz, 1H), 7.28 (t, J=7 Hz, 1H), 7.19 (bs, 1H), 7.03 (dt, J=18 and 7 Hz, 1H), 5.88 (d, J=18 Hz, 1H), 4.19 (q, J=7 Hz, 2H), 2.87 (t, J=7 Hz, 2H), 2.63 (m, 2H), 2.61 (s, 3H), 1.28 (t, J=7 Hz, 3H).

EXAMPLE 28

Preparation of
N-Benzyl-3-[2-(indol-3-yl)ethyl]β-alanine ethyl ester (33)

A mixture of olefin 32 (5.0 g, 17.5 mmol) and benzylamine (7.7 mL, 70 mmol) was heated at 80° C. for 20 hours. The cooled reaction mixture was applied directly to a flash chromatography column (silica, 30% ethyl acetate/hexanes) to give the Micheal adduct 33 (4.9 g) as a viscous yellow oil.

TLC Rf=0.43 (40% ethyl acetate/hexanes).

EXAMPLE 29

Preparation of 3-[2-(indol-3-yl)ethyl]δ-alanine ethyl ester.pTSA salt (34)

A mixture of the benzylamine 33 (4.6 g, 11.7 mmol), 10% Pd/C (2.3 g), and p-toluenesulfonic acid (pTSA)(2.2 g, 11.7 mmol) was stirred at ambient temperature under a hydrogen atmosphere (1 atm) for 4 hours. The reaction was then purged with argon, filtered through a celite pad and concentrated. The resulting foam was triturated with 50% ether/pet. ether to give the salt 34 (4.8 g) as a white solid.

TLC Rf=0.22 (9:1:1 CH$_2$Cl$_2$/CH$_3$OH/AcOH); $^1$H NMR (CD$_3$OD) δ7.70 (d, J=8 Hz, 2H), 7.53 (d, J=7 Hz, 1H), 7.32 (d, J=7 Hz, 1H), 7.20 (d, J=8 Hz, 2H), 7.06 (t, J=7 Hz, 1H), 7.05 (s, 1H), 6.99 (t, J=7 Hz, 1H), 4.15 (q, J=7 Hz, 1H), 3.56 (m, 1H), 2.85 (m, 3H), 2.65 (m, 1H), 2.33 (s, 3H), 2.05 (m, 2H), 1.22 (t, 7 Hz, 3H).

EXAMPLE 30

Preparation of N-BOC-Pib-Gly ethyl ester (35)

To a stirred solution of the carboxylic acid 14 (4.0 g, 14.7 mmol), NMM (1.6 mL, 14.7 mmol), and ethyl acetate (200 mL) at −15° C. was added isobutyl chloroformate (1.9 mL, 14.7 mmol). After 15 minutes glycine ethyl ester.HCl (4.1 g, 29 mmol) and NMM (4.8 mL, 45 mmol) were added. After 45 minutes the reaction mixture was washed with H$_2$O, sat. NaHCO$_3$ and brine, dried (MgSO$_4$) and concentrated. Flash chromatography (silica, 60% ethyl acetate/hexanes) to yield the dipeptide 35 (5.0 g) as a colorless oil. TLC Rf=0.60 (ethyl acetate); $^1$H NMR (CDCl$_3$) δ5.98 (m, 1H), 4.22 (q, J=7 Hz, 2H), 4.08 (m, 2H), 4.05 (d, J=5 Hz, 2H), 2.68 (m, 2H), 2.24 (t, J=7 Hz, 2H), 1.70 (m, 4H), 1.47 (s, 9H), 1.30 (t, J=7 Hz, 3H) 1.10 (m, 2H).

EXAMPLE 31

Preparation of N-BOC-Pib-Gly (36)

A mixture of ester 35 (5.0 g, 14 mmol), 1N NaOH (21 mL, 21 mmol), and CH$_3$OH (100 mL) was stirred at ambient temperature for 3 hours. The reaction mixture was then concentrated to dryness, dissolved in H$_2$O, and acidified with 5% KHSO$_4$ (pH∼3.0). Extraction with ethyl acetate followed by washing the ethyl acetate with brine, drying (MgSO$_4$), and concentrating gave the carboxylic acid 36 (4.2 g) as a colorless solid.

TLC Rf=0.50 (9:0.5:0.5 CH$_2$Cl$_2$/CH$_3$OH/AcOH).

EXAMPLE 32

Preparation of
N-BOC-Pib-Gly-3-[2-(indol-3-yl)ethyl]β-alanine ethyl ester (37)

To a stirring solution of the carboxylic acid 36 (415 mg, 1.5 mmol), the amine 34 (600 mg, 1.4 mmol), HOBT (280 mg, 2.1 mmol), NMM (0.5 mL, 4.6 mmol), and dry DMF (7 mL) at ambient temperature was added EDC (370 mg, 2.0 mmol). After 20 hours the reaction mixture was diluted with ethyl acetate and then washed with H$_2$O, sat. NaHCO$_3$, 5% KHSO$_4$ and brine, dried (MgSO$_4$), and concentrated. Flash chromatography (silica, 95% ethyl acetate/hexanes) gave the tripeptide 37 (135 mg) as a solid.

TLC Rf=0.17 (ethyl acetate); $^1$H NMR (CDCl$_3$) δ8.20 (bs, 1H), 7.57 (d, J=7 Hz, 1H), 7.36 (d, J=7 Hz, 1H), 7.28 (t, J=7 Hz, 1H), 7.11 (t, J=7 Hz, 1H), 7.01 (s, 1H), 6.67 (d, J=8 Hz, 1H), 6.20 (t, J=4 Hz, 1H), 4.35 (m, 1H), 4.14 (q, J=7 Hz, 2H), 4.10 (m, 2H), 3.83 (m, 2H), 2.80 (m, 2H), 2.65 (m, 2H), 2.54 (d, J=6 Hz, 2H), 2.20 (t, J=7 Hz, 2H), 1.95 (m, 2H), 1.80–1.00 (m, 9H), 1.48 (s, 9H), 1.24 (t, J=7 Hz, 3H).

EXAMPLE 33

Preparation of
N-BOC-Pib-Gly-3-[2-(indol-3-yl)ethyl]β-alanine (38)

A mixture of the ester 37 (135 mg, 0.24 mmol), 1N NaOH (0.5 mL, 0.5 mmol), and CH$_3$OH (5 mL) was stirred at ambient temperature for 20 hours. The reaction mixture was then concentrated to dryness, dissolved in H$_2$O, and then acidified to pH~3.0 with 5% KHSO$_4$. The aqueous solution was extracted with ethyl acetate and the organic portion washed with brine, dried (MgSO$_4$), and concentrated to give the carboxylic acid 38 (110 mg) as a white solid.

TLC Rf=0.55 (9:1:1 CH$_2$Cl$_2$/CH$_3$OH/AcOH).

EXAMPLE 34

Preparation of Pib-Gly-3-[2-(indol-3-yl)ethyl]βalanine (39)

To a stirred solution of 38 (110 mg, 0.20 mmol) CH$_2$Cl$_2$ (5 mL), and anisole (45 μL, 0.40 mmol) at 0° C. was added trifluoroacetic acid (5 mL). After 1 hour the reaction mixture was concentrated. Flash chromatography (silica, 10:1:1 ethanol/NH$_4$OH/H$_2$O) gave the amino acid 39 (61 mg) as foam.

TLC Rf=0.15 (10:1:1 ethanol/NH$_4$OH/H$_2$O); $^1$H NMR (D$_2$O) δ7.52 (d, J=8 Hz, 1H), 7.34 (d, J=8 Hz, 1H), 7.08 (t, J=8 Hz, 1H), 7.03 (s, 9H), 7.00 (t, J=8 Hz, 1H), 4.05 (m, 1H), 3.62 (s, 2H), 3.10 (m, 2H), 2.60 (m, 4H), 2.25 (d, J=5 Hz, 2H), 2.13 (t, J=7 Hz, 2H), 1.90–1.00 (m, 11H).

EXAMPLE 35

Preparation of
N-(R)-α-Methylbenzyl-3(R)-[2-(indol-3-yl)ethyl]β-alanine ethyl ester (33a) and
N-(R)-α-Methylbenzyl-3-(S)-[2-(indol-3-yl)ethyl]β-alanine ethyl ester (33b)

A mixture of olefin 32 (2.77 g, 9.7 mmol) and R-(+)-α-methylbenzylamine (5.03 mL, 39 mmol) was heated under a cold finger at 110° C. for 40 hours. The cooled reaction mixture was applied directly to a flash chromatography column (silica, 40:2:1, hexanes:ethyl acetate: 2-propanol). The (R,R) isomer 33a eluted first (1.19 g) as a viscous yellow oil which solidified on standing. Recrystallization from hexanes/ethyl acetate provided crystalline material. The (R,S) isomer 33b eluted next (1.55 g) as a viscous yellow oil containing ca 10% of the (R,R) isomer. 33a: Rf=0.52 (60% EtOAc/hexanes);

$^1$H NMR (400 MHz, CDCl$_3$) δ7.84 (br s, 1H), 7.52 (dd, J=7.9, 0.7 Hz, 1H), 7.20–7.35 (m, 6H), 7.16 (tm, J=7.1, 1.3 Hz, 1H), 7.08 (tm, J=7.3, 1.1 Hz, 1H), 6.70 (br d, J=2.4 Hz, 1H), 4.10 (q, J=7.1 Hz, 2H), 3.90 (q, J=6.6 Hz, 1H), 2.80–2.90 (m, 2H), 2.68 (ABX dt, J=16, 7.9 Hz, 1H), 2.53 (ABX dd, J=14.5, 5.9 Hz, 1H), 2.42 (ABX dd, J=14.6, 5.3 Hz, 1H), 1.79 (q, J=7.5 Hz, 2H), 1.33 (d, J=6.4 Hz, 3H), 1.22 (t, J=7.1 Hz, 3H). 33b: Rf=0.42 (60% EtOAc/hexanes);

$^1$H NMR (400 MHz, CDCl$_3$) δ7.95 (br s, 1H), 7.57 (dd, J=7.5, 0.7 Hz, 1H), 7.34 (dm, J=8.1, 0.7 Hz, 1H), 7.17–7.30 (m), 7.11 (tm, J=7.9, 0.9 Hz, 1H), 6.89 (br d, J=2.2 Hz, 1H), 4.02–4.15 (ABX m, 2H), 3.89 (q, J=6.6 Hz, 1H), 2.95 (m, 1H), 2.82 (ABX ddd, J=15, 9.7, 5.9 Hz, 1H), 2.69 (ABX ddd, J=15, 9.7, 6.0 Hz, 1H), 2.47 (ABX dd, J=15.0, 5.1 Hz, 1H), 2.40 (ABX dd, J=15.0, 7.7 Hz, 1H), 1.96 (m, 1H), 1.83 (m, 1H), 1.30 (d, J=6.6 Hz, 3H), 1.21 (td, J=7.1, 0.7 Hz, 3H).

EXAMPLE 36

Preparation of 3(R)-[2-(indol-3-yl)ethyl]β-alanine ethyl ester (34a)

Amine 33a (996 mg, 2.74 mmol) was dissolved in 10 mL EtOH. After addition of Pearlman's catalyst (20% Pd(OH)$_2$/C, 128 mg) the flask was charged with hydrogen and maintained at balloon pressure. After 16 hours an additional portion of catalyst was added (122 mg) along with fresh H$_2$. Four hours later the sample was filtered through celite and concentrated to provide amine 34a (707 mg, 99%, ca 95% pure).: Rf=0.22 (10:1, NH$_3$ satd. CHCl$_3$:EtOAc);

$^1$H NMR (400 MHz, CDCl$_3$). δ8.01 (br s, 1H), 7.60 (dt, J=8.9, 0.4 Hz, 1H), 7.35 (dt, J=8.1, 0.9 Hz, 1H), 7.19 (td, J=7.1, 1.3 Hz, 1H), 7.11 (td, J=7.1, 1.2 Hz, 1H), 6.99 (br d, J=2.2 Hz, 1H), 4.15 (q, J=7.1 Hz, 2H), 3.72 (q, J=7.0 Hz, 1H), 3.29 (m, 1H), 2.92–2.78 (m, 2H), 2.53 (ABX dd, J=15.6, 4.0 Hz, 1H), 2.33 (ABX dd, J=15.6, 8.8 Hz, 1H), 1.92–1.73 (m, 2H), 1.25 (q, J=7.1 Hz, 3H).

EXAMPLE 37

Preparation of
N-Boc-Pib-Gly-3(R)-[2-(indol-3-yl)ethyl]β-alanine ethyl ester (37a)

To a stirring solution of carboxylic acid 36 (280 mg, 0.85 mmol), amine 34a (214 mg, 0.82 mmol), HOBT (150 mg, 1.11 mmol), and Et$_3$N (0.36 mL, 2.59 mmol) in 3 mL dry DMF at 0° C. was added EDC (215 mg, 1.12 mmol). After slowly warming to ambient temperature for 16 hours the reaction mixture was diluted with ethyl acetate, washed with water, and the aqueous phase was re-extracted with fresh ethyl acetate. The combined organic portions were washed with water, 5% KHSO$_4$, sat. NaHCO$_3$, and brine, dried (MgSO$_4$), and concentrated. Flash chromatography (silica, ethyl acetate) gave the protected tripeptide 37a (354 mg, 76%) as a white solid.: Rf=0.19 (ethyl acetate);

$^1$H NMR (300 MHz, CDCl$_3$) δ8.07 (br s, 1H), 7.57 (d, J=7.8 Hz, 1H), 7.36 (d, J=8.0 Hz, 1H), 7.19 (td, J=7.1, 1.0 Hz, 1H), 7.11 (td, J=7.9, 1.2 Hz, 1H), 7.03 (br d, J=2.2 Hz, 1H), 6.47 (d, J=9.3 Hz, 1H), 6.00 (br t, J=7 Hz, 1H), 4.35 (m, 1H), 4.12 (q, J=7.2 Hz, 2H), 4.15–4.0 (br m, 2H), 3.87 (ABX dd, J=15, 5.2 Hz, 1H), 3.79 (ABX dd, J=15, 4.9 Hz, 1H), 2.80 (td, J=7.3, 2.6 Hz, 2H), 2.64 (br t, J=12 Hz, 2H), 2.55 (d, J=4.9 Hz, 2H), 2.19 (t, J=7.5 Hz, 2H), 1.98 (m, 2H), 1.7–1.6 (m, 4H), 1.45 (s, 9H), 1.35 (m), 1.24 (t, J=7.0 Hz, 3H), 1.05 (qd, J=12.2, 4.1 Hz, 2H).

EXAMPLE 38

Preparation of
N-Boc-Pib-Gly-3(R)-[2-(indol-3-yl)ethyl]β-alanine (38a)

Ester 37a (494 mg, 0.87 mmol) was dissolved in 10 mL MeOH and aq. NaOH (2N, 0.87 mL, 1.64 mmol) was added. After stirring for 16 hours additional NaOH (2N, 0.43 mL, 0.86 mmol) was added and the reaction was allowed to continue for 24 hours more. Following evaporation of the solvent, the residue was treated with water and 5% KHSO₄ until pH <2, extracted twice with ethyl acetate, and the combined organics were washed with brine, dried (MgSO₄) and concentrated providing acid 38a (463 mg, 98%).: Rf=0.30 (19:1:1 CH₂Cl₂:MeOH:HOAc);

$^1$H NMR (400 MHz, CDCl₃) δ8.04 (br s, 1H), 7.57 (dd, J=7.1, 0.4 Hz, 1H), 7.35 (d, J=8.1 Hz, 1H), 7.19 (t, J=6.8 Hz, 1H), 7.10 (t, J=7.3 Hz, 1H), 6.99 (br d, J=2.2 Hz, 1H), 6.81 (br d, J=9.0 Hz, 1H), 6.39 (br s, 1H), 4.37 (m, 1H), 4.05 (br s, 2H), 3.91 (ABX dd, J=16.7, 5.1 Hz, 1H), 3.84 (ABX dd, J=16.5, 5.5 Hz, 1H), 2.81 (br q, J=6 Hz, 2H), 2.68-2.58 (m, 2H), 2.62 (ABX dd, J=16, 4.6 Hz, 1H), 2.53 (ABX dd, J=15.9, 6.0 Hz, 1H), 2.19 (br t, J=7.1 Hz, 2H), 2.06-1.92 (m, 2H), 1.68-1.56 (m, 4H), 1.45 (s, 9H), 1.38 (m), 1.29-1.21 (m, 4H), 1.08 (qd, J=12.4, 4.0 Hz, 2H).

EXAMPLE 39

Preparation of Pib-Gly-3(R)-[2-(indol-3-yl)ethyl]β-alanine hydrogen chloride salt (39a)

HCl gas (lecture bottle) was bubbled vigorously through a mechanically stirred solution of 38a (3.7 g, 6.8 mmol), anisole (1.0 mL), and ethyl acetate (200 mL) at −20° C. Initially (approximately 2 min), a white precipitate formed. However, it turned from a solid to a gum after an additional 2 min. HCl gas was passed through the solution for another 10 minutes with the internal temperature rising to 5° C., however, the gum remained, even upon addition of CH₂Cl₂ (100 mL). TLC analysis of the solution indicated no 38a remained. Argon was then passed through the reaction mixture for 1.0 hour without cooling. After 1.0 hour a white suspension containing some large pieces of hardened gum remained. The solids were filtered and washed with EtOAc (3×100 mL). The solid was ground and then triturated with acetonitrile (50 mL) then collected by filtration to remove a small amount of 38along with other impurities providing 39a (3.1 g, 6.5 mmol, 95%) as an ivory solid.

TLC Rf=0.19 (10:1:1 ethanol/conc. NH₄OH/H₂O); $^1$H NMR (300 MHz, D₂O) δ7.66 (d, J=7 Hz, 1H), 7.50 (d, J=7 Hz, 1H), 7.23 (t, J=7 Hz, 1H), 7.17 (s, 1H), 7.15 (t, J=7 Hz, 1H), 4.23 (m, 1H), 2.78 (s, 2H), 3.29 (m, 2H), 2.78 (m, 4H), 2.58 (m, 2H), 2.29 (t, J=6 Hz, 2H), 2.05-1.17 (m, 11H).

EXAMPLE 40

Preparation of N-(S)-α-Methylbenzyl-3(S)-[2-(indol-3-yl)ethyl]β-alanine ethyl ester (33c) and N-(S)-α-Methylbenzyl-3(R)-[2-(indol-3-yl)ethyl]β-alanine ethyl ester (33d)

Prepared as for 33a and 33b by heating olefin 32 (1.00 g, 3.5 mmol) and S-(−)-α-methylbenzylamine (1.8 mL, 14 mmol) at 100° C. for 64 hours, providing 33c (396 mg, 28%) and 33d (484 mg, 34%). 33c: [α]$_D$ −30.3° (c=0.0148 g/mL, CHCl₃). 33d: [α]$_D$ −53.7° (c=0.01185 g/mL, CHCl₃).

EXAMPLE 41

Preparation of 3(S)-[2-(indol-3-yl)ethyl]β-alanine ethyl ester.p-TSA salt (34c)

Prepared as for 34 from 33c (257 mg, 0.63 mmol), p-TSA (122 mg, 0.63 mmol) and 10% Pd/C (70 mg) in 5 mL MeOH. This produced 34c (290 mg) as a tan solid.

EXAMPLE 42

Preparation of N-Boc-Pib-Gly-3(S)-[2-(indol-3-yl)ethyl]β-alanine ethyl ester (37c)

A suspension of acid 36 (207 mg, 0.63 mmol) in 2 mL ethyl acetate was cooled to −10° C. After addition of NMM (69 µL, 0.63 mmol) and isobutyl chloroformate (82 µL, 0.63 mmol) the reaction proceeded for 20 minutes. In a second flask also at −10° C. amine salt 34c (290 mg, 0.63 mmol) and NMM (207 µL, 1.89 mmol) were suspended in 4 mL ethyl acetate then added to the mixed anhydride. After 2.5 hours the mixture was quenched with water, extracted twice with ethyl acetate, the combined organic layers were washed with 5% KHSO₄, sat. NaHCO₃, and brine, dried (MgSO₄), concentrated. Flash chromatography (silica, 90% ethyl acetate: hexanes) gave the protected tripeptide 37c (163 mg, 45%) as a foamy solid.

EXAMPLE 43

Preparation of N-Boc-Pib-Gly-3(S)-[2-(indol-3-yl)ethyl]β-alanine (38c)

Ester 37c (163 mg, 0.29 mmol) was dissolved in 5 mL MeOH and aq. NaOH (1N, 0.58 mL, 0.58 mmol) was added. After stirring for 16 hours the solvent was evaporated and the residue was treated with water and 5% KHSO₄ until pH <2, extracted with CHCl₃ and the organic layer was washed with brine, dried (MgSO₄) and concentrated providing acid 38c (168 mg).

EXAMPLE 44

Preparation of Pib-Gly-3(S)-[2-(indol-3-yl)ethyl]β-alanine (39c)

To a stirred solution of 38c (168 mg, 0.31 mmol) in 5 mL CH₂Cl₂, anisole (67 µL, 0.62 mmol), and dimethylsulphide (114 µL, 1.55 mmol) at 0° C. was added TFA (5 mL). After 1 hour the solvents were removed and the residue was chromatographed on silica (10:1:1, EtOH:-H₂O:NH₄OH). Preparative HPLC purification (DeltaPak C18, H₂O/CH₃CN/TFA) provided 39c as a TFA salt.

Rf=0.16 (10:1:1 EtOH:conc NH₄OH:H₂O): $^1$H NMR (400 MHz, D₂O) δ7.57 (d, J=7.8 Hz, 1H), 7.40 (d, J=8.0 Hz, 1H), 7.14 (t, J=7.1 Hz, 1H), 7.08 (s, 1H), 7.05 (t, J=7.1 Hz, 1H), 4.11 (brs, 1H), 3.68 (s, 2H), 3.18 (br d, J=12.8 Hz, 2H), 2.74-2.62 (m, 4H), 2.44 (br s, 2H), 2.19 (t, J=7.1 Hz, 2H), 1.91 (m, 1H), 1.78 (m, 1H), 1.72-1.63 (m, 2H), 1.49 (m, 2H), 1.30 (m, 1H), 1.18-1.06 (m, 4H).

EXAMPLE 45

Preparation of N-Boc-Pib-Sar-ethyl ester (40)

Utilizing the procedure for converting 14 to 35, 14 (500 mg, 1.8 mmol) gave 40 (610 mg, 1.6 mmol) as a colorless oil.

TLC Rf=0.65 (ethyl acetate); $^1$H NMR (300 MHz, CDCl₃) δ4.23 (m, 2H), 4.14 (s, 1.5H), 4.10 (m, 2H), 4.05

(s, 0.5H), 3.11 (s, 2H), 3.01 (s, 1H), 2.70 (m, 2H), 2.40 (t, J=6 Hz, 1.5H), 1.70 (m, 4H), 1.49 (s, 9H), 1.50–1.00 (m, 5H), 1.32 (m, 3H).

EXAMPLE 46

Preparation of N-Boc-Pib-Sar (41)

Utilizing the procedure for converting 37 to 38, 40 (600 mg, 1.6 mmol) gave 41 (570 mg, 1.6 mmol) as a colorless oil.

TLC Rf=0.72 (9:1:1 $CH_2Cl_2/CH_3OH/AcOH$).

EXAMPLE 47

Preparation of N-Boc-Pib-Sar-3(R)-[2-(indol-3-yl)ethyl]β-alanine ethyl ester (42)

Utilizing the procedure for converting 14 to 35, 41 (150 mg, 0.44 mmol) was reacted with 34a (140 mg, 0.53 mmol) to give 42 (80 mg, 0.18 mmol) after flash chromatography (silica, 80% ethyl acetate/hexanes then ethyl acetate).

TLC Rf=0.25 (ethyl acetate); $^1$H NMR (300 MHz, $CDCl_3$) δ8.20 (m, 1H), 7.67 (m, 1H), 7.38 (d, J=7 Hz, 1H), 7.20 (t, J=7 Hz, 1H), 7.12 (t, J=7 Hz, 1H), 7.05 (s, 1H), 6.76 (d, J=10 Hz, 0.75H), 6.66 (d, J=10 Hz, 0.25H), 4.30 (m, 1H), 4.12 (m, 2H) 4.05 (m, 2H), 4.02 (s, 2H), 3.10 (s, 2.25H), 2.97 (s, 0.75H), 2.85–2.50 (m, 6H), 2.38 (t, J=7 Hz, 1.5H), 2.25 (t, J=7 Hz, 0.5H), 2.00–1.00 (m, 11H), 1.48 (s, 9H), 1.28 (m, 3H).

EXAMPLE 48

Preparation of N-Boc-Pib-Sar-3(R)-[2-(indol-3-yl)ethyl]β-alanine (43)

Utilizing the procedure for converting 37 to 38, 42 (80 mg, 0.14 mmol) gave 43 (80 mg, 0.14 mmol) as a colorless foam.

TLC Rf=0.41 (9:0.5:0.5 $CH_2Cl_2/CH_3OH/AcOH$).

EXAMPLE 49

Preparation of Pib-Sar-3(R)-[2-(indol-3-yl)-ethyl]β-alanine (44)

To a stirred solution of 43 (80 mg, 0.14 mmol) in $CH_2Cl_2$ (2 mL) at −15° C. was added TFA (2 mL). After 1 hour the reaction mixture was concentrated and the residual TFA removed azeotropically with toluene. Flash chromatography (silica, 10:0.5:0.5 $CH_3OH/NH_4OH/H_2O$) gave 44 (10 mg, 22 μmol) as a colorless glass.

Rf=0.29 (10:1:1 $CH_3OH/NH_4OH/H_2O$); $^1$H NMR (300 MHz, $CD_3OD$) δ7.52 (m, 1H), 7.28 (m, 1H), 7.08–6.90 (m, 3H), 4.30 (m, 1H), 4.02 (m, 2H), 3.21 (m, 2H), 3.11 (s, 1.8H), 2.95 (s, 1.2H), 3.00–2.70 (m, 4H), 2.43 (m, 3H), 2.30 (m, 1H), 2.00–1.20 (m, 11H).

EXAMPLE 50

Preparation of N-Boc-Pib-4(R)-benzyl-2-oxazolidinone (45)

To a stirred solution of 14 (2.0 g, 7.4 mmol), NEt$_3$ (1.2 mL, 8.9 mmol) and dry THF (40 mL) at −78° C. was added trimethylacetyl chloride (0.96 mL, 7.8 mmol). After 10 minutes the resulting white suspension was warmed to 0° C. and stirred for 30 minutes. The reaction mixture was then recooled to −78° C. and treated with (R)-(+)-4-benzyl-2-oxazolidinone lithium (45 mL, 6.8 mmol, 0.15M in THF); prepared by addition of n-BuLi (4.4 mL, 6.8 mmol, 1.6M/hexanes) to solution of (R)-(+)-4-benzyl-2-oxazolidinone (1.2 g, 6.8 mmol) in THF (40 mL) at −78° C. After addition was complete the reaction mixture was warmed to 0° C. for 1.0 hour, followed by quenching with sat. NH$_4$Cl (25 mL), then concentration. The residue was diluted with EtOAc and then washed with H$_2$O, 1N NaOH, 5% KHSO$_4$ and brine, dried (MgSO$_4$) and concentrated. Flash chromatography (silica, 15% EtOAc/hexanes) gave 45 (3.0 g, 94%) as a colorless oil.

TLC R$_f$=0.42 (30% EtOAc/hexanes); $^1$H NMR (CDCl$_3$) δ7.5–7.2 (m, 5H), 4.70 (m, 1H), 4.22 (m, 2H), 4.12 (m, 2H), 3.34 (dd, J=13 and 3 Hz, 1H) 2.97 (m, 2H), 2.82 (m, 1H), 2.73 (m, 2H), 1.75 (m, 4H), 1.49 (s, 9H), 1.40 (m, 2H), 1.15 (m, 2H).

EXAMPLE 51

Preparation of [2(S)-(propen-2-yl)-4-(N-Boc-piperidin-4-yl)]-butanoyl-4(R)-benzyl-2-oxazolidinone (46)

To a stirred solution of 45 (2.5 g, 5.8 mmol) in THF (50 ml) at −78° C. was added lithium bis(trimethylsilyl)amide (7.0 mL, 7.0 mmol, 1M/hexanes) followed by allyl bromide (2.5 mL, 29 mmol). The cooling bath was then removed and the reaction stirred at 0° C. for 1.5 hours. The reaction was quenched with sat. NH$_4$Cl, then diluted with EtOAc followed by washing with sat. NaHCO$_3$, 5% KHSO$_4$, and brine, drying (MgSO$_4$) and concentration. Flash chromatography (silica, 15% EtOAc/hexanes) afforded 46 (1.8 g, 66%) as a colorless oil.

TLC R$_f$=0.53 (30% EtOAc/hexanes); $^1$H NMR (CDCl$_3$) δ 7.40–7.20 (m, 5H), 5.82 (m, 1H), 5.10 (m, 2H), 4.80 (m, 1H), 4.20 (m, 2H), 4.07 (m, 2H), 3.90 (m, 1H), 3.31 (dd, J=13 and 3 Hz, 1H), 2.68 (m, 2H), 2.48 (m, 1H), 2.35 (m, 1H), 1.90–1.20 (m, 7H), 1.47 (s, 9H), 1.10 (m, 2H).

EXAMPLE 52

Preparation of [2(S)-(propen-2-yl)-4-(N-Boc-piperidin-4-yl)]-butanoic acid (47)

To a stirred solution of 46 (1.8 g, 3.8 mmol), 30% H$_2$O$_2$ (8.5 mL, 83 mmol), THF (41 mL) and H$_2$O (12 mL) at ambient temperature was added LiOH (14 mL, 14 mmol, 1N). After 2 h the excess LiOH was quenched with 10% NaHSO$_4$ dropwise at 0° C. The reaction was then acidified with 5% KHSO$_4$ and extracted with EtOAc. The EtOAc portion was then washed with brine, dried (MgSO$_4$), and concentrated to give 47 (0.37 g) as a colorless oil.

TLC R$_f$=0.79 (10% CH$_3$OH/EtOAc).

EXAMPLE 53

Preparation of [2(S)-(propen-2-yl)-4-(N-Boc-piperidin-4-yl)]-butanoyl-Sar(ethyl ester) (48)

To a stirred suspension of 47 (350 mg, 1.1 mmol), sarcosine ethyl ester.HCl (870 mg, 5.6 mmol), HOBT (180 mg, 1.3 mmol), NEt$_3$ (0.47 mL, 3.3 mmol) and DMF (10 mL) at −15° C. was added EDC (260 mg, 1.3 mmol) followed by removal of the cooling bath. After 3.5 hours the reaction mixture was diluted with EtOAc and then washed with H$_2$O, sat. NaHCO$_3$, 5% KHSO$_4$ and brine, dried (MgSO$_4$) and concentrated. Flash chromotography (silica, 30% EtOAc/hexanes) to give 48 (210 mg, 47%) as an oil.

TLC R$_f$=0.83 (EtOAc); $^1$H NMR (CDCl$_3$) δ5.82 (m, 1H), 5.10 (m, 2H), 4.20 (m, 4H), 4.10 (m, 2H), 3.15 (s, 0.9H), 3.05 (s, 0.1H), 2.78 (m, 1H), 2.70 (m, 2H), 2.45 (m, 1H), 2.22 (m, 2H), 1.80–1.00 (m, 9H), 1.48 (s, 9H), 1.31 (t, J=7 Hz, 3H).

EXAMPLE 54

Preparation of
[2(S)-(propen-2-yl)-4-(N-Boc-piperidin-4-yl)]-butanoyl-Sar (49)

To a stirred solution of 48 (200 mg, 0.49 mmol) THF (5 mL), ethanol (10 mL), and H$_2$O (0.5 mL) was added LiOH (60 mg, 1.5 mmol). After 2.5 hours the reaction mixture was concentrated, then acidified with 5% KHSO$_4$. The aqueous solution was extracted with EtOAc and then the organic portion was washed with brine, dried (MgSO$_4$), and concentrated to give 49 (190 mg, quantitative).

TLC R$_f$=0.40 (9:0.5:0.5 CH$_2$Cl$_2$/HOAc/CH$_3$OH).

EXAMPLE 55

Preparation of
[2(S)-(propen-2-yl)-4-(N-Boc-piperidin-4-yl)]-butanoyl-Sar-3(R)-(2-phenethyl)β-alanine methyl ester (50)

Compound 49 (190 mg, 0.50 mmol) was converted to 50 (260 mg, 91%) after flash chromatography (silica, 60% EtOAc/hexanes) using the same procedure for converting 47 to 48.

TLC R$_f$=0.69 (EtOAc); $^1$H NMR (CDCl$_3$) δ7.35–7.10 (m, 5H), 6.70 (m, 1H), 5.78 (m, 1H), 5.05 (m, 2H), 4.30 (m, 1H), 4.17 (d, J=16 Hz, 1H), 4.05 (m, 2H), 3.90 (d, J=16H, 1H), 3.68 (s, 3H), 3.17 (s, 0.8H), 3.01 (s, 0.2H), 2.80–2.40 (m, 8 h), 2.23 (m, 1H), 1.90–1.00 (m, 11H), 1.48 (s, 9H).

EXAMPLE 56

Preparation of
[2(R)-propyl-4-(N-Boc-piperidin-4-yl)]-butanoyl-Sar-3(R)-(2-phenethyl)β-alanine methyl ester (51)

A mixture of 50 (130 mg, 0.23 mmol), 10% Pd/C (65 mg), and ethanol (2.5 mL) was stirred under a hydrogen atmosphere for 24 hours. The reaction mixture was then filtered through a celite pad and the filtrate concentrated to give 51 (130 mg, quantitative) as an oil.

TLC R$_f$=0.69 (EtOAc); $^1$H NMR (CDCl$_3$) δ7.30 (m, 2H), 7.20 (m, 3H), 6.80 (d, J=10 Hz, 1H), 4.32 (m, 1H), 4.13 (d, J=16 Hz, 1H), 4.07 (m, 1H), 3.95 (d, J=16 Hz, 1H), 3.70 (s, 3H), 3.19 (s, 0.9H), 3.02 (s, 0.1H) 2.75–2.55 (m, 5H), 1.85 (m, 1H), 1.70–1.00 (m, 1H), 1.48 (s, 9H), 0.94 (t, J=7Hz, 3H).

EXAMPLE 57

Preparation of
[2(R)-propyl-4-(N-Boc-piperidin-4-yl)]butanoyl-Sar-3(R)-(2-phenethyl)β-alanine (52)

To a stirred solution of 51 (130 mg, 0.23 mmol), THF (1mL), CH$_3$OH (2 mL) and H$_2$O (1 mL) was added 1N LiOH (0.7 mL, 0.7 mmol). After 2.0 hours the reaction mixture was concentrated. Acidification with 5% KHSO$_4$ was followed by extraction with EtOAc. The EtOAc portion was washed with brine, dried (MgSO$_4$), and concentrated to yield 52 (125 mg, 97%). TLC R$_f$=0.50 (9:0.5:0.5 CH$_2$Cl$_2$/CH$_3$OH/HOAc).

EXAMPLE 58

Preparation of
[2(R)-propyl-4-(piperidin-4-yl)]butanoyl-Sar-3(R)-(2-phenethyl)β-alanine (53)

To a stirred solution of 52 (125 mg, 0.22 mmol) and CH$_2$Cl$_2$ (2.5 mL) at ambient temperature was added TFA (2.5 mL). After 1.5 hours the reaction mixture was concentrated and the residue purified by flash chromatography (silica, 10:0.4:0.4 CH$_3$OH/NH$_4$OH/H$_2$O) to give 53 (110 mg, 92%) as a white solid.

TLC R$_f$=0.48 (10:1:1 CH$_3$OH/NH$_4$OH/H$_2$O); $^1$H NMR (CD$_3$OD) δ7.30–7.10 (m, 5H), 4.45 (m, 1H), 4.27 (m, 0.4H), 4.18 (m, 0.6H), 3.83 (d, J=16 Hz, 0.4H), 3.64 (d, J=16 Hz, 0.6H), 3.30 (m, 2H), 3.19 (s, 1.8H), 3.00 (s, 1.2H), 2.88 (m, 2H), 2.65 (m, 2H), 2.35 (m, 2H), 2.35 (m, 2H), 2.00–1.20 (m, 15H), 0.90 (t, J=7 Hz, 3H).

EXAMPLE 59

Preparation of Methyl 2,3-diaminopropanoate (55)

A stirred solution of methanol (200 ml) at 5° was treated with thionyl chloride (65.2 g, 40 ml, 0.54 moles) dropwise over 0.5 hr. Then 2(S),3-diaminopropanoic acid (10.0 g, 0.071 moles) was added and the reaction mixture was warmed to room temperature and then refluxed overnight. The solvent was then removed to provide 55 as a white solid. R$_f$ 0.6 silica gel, EtOH/NH$_4$OH/H$_2$O 10:1:1.

EXAMPLE 60

Preparation of N-BOC-Aha-Gly-2-amino-β-alanine methyl ester (56)

A stirred solution of 36 (1.0 g, 3.0 mmoles) in DMF (30 ml) at −15° was treated with isobutyl chloroformate (0.58 ml, 4.5 mmoles) and the reaction mixture was stirred for 20 minutes. Then, 55 (0.7 g, 4.5 mmoles) was added followed by N-methylmorpholine (0.5 ml, 4.5 mmoles). The reaction mixture was stirred at −15° for 1 hr and then at room temp overnight. The reaction mixture was concentrated, diluted with saturated aq. NaHCO$_3$ soln. and extracted with EtOAc. The organic phase was separated, washed with brine, dried (Na$_2$SO$_4$) and concentrated to provide 56 as an oil. R$_f$ 0.19, silica gel, CH$_2$Cl$_2$/MeOH/HOAc, 9:1:1.

EXAMPLE 61

Preparation of
N-Boc-Aha-Gly-2(S)-n-butylsulfonylamino-β-alanine methyl ester (57)

A stirred solution of 56 (2.5 g, 5.8 mmoles) in CHCl$_3$ (20 ml) at 25° was treated with pyridine (1.4 ml, 17.4 mmoles) followed by n-butylsulfonyl chloride (2.2 ml, 17.4 mmoles), and the resulting mixture was stirred for 20 hrs. The reaction was then diluted with EtOAc and washed with H$_2$O, 10% KHSO$_4$ solution, brine and then dried (Na$_2$SO$_4$) and concentrated. The residue was purified by flash chromatography on silica gel eluting with CH$_2$Cl$_2$/MeOH/HOAc, 9/0.25/0.25 to provide pure 56 as an oil. R$_f$ 0.61 CH$_2$Cl$_2$/MeOH/HOAc, 9/0.5/0.5.

$^1$H NMR (300 MHz, CDCl$_3$) δ0.95 (3H, t), 1.07 (2H, m), 1.27 (3H, m), 1.45 (9H, 5), 1.67 (4H, m), 1.79 (2H, m), 2.37 (2H, m), 2.69 (2H, bt), 3.03 (2H, t), 3.18 (2H, m), 3.80 (3H, 5), 3.98 (1H, dd), 4.08 (2H, m), 4.26 (1H, m), 5.99 (1H, dd), 7.06 (1H, bt), 7.20 (1H, bt).

Pib-Gly-2-n-butylsulfonylamino-β-alanine (58)

A solution of 56 (1.0 g, 3.1 mmoles) in EtOH (30 ml) at room temperature was treated with 1N NaOH (12.5 ml) and the resulting solution was stirred for 1 hr. The reaction mixture was then diluted with EtOAc and acidified with 10% aq. KHSO₄ solution. The organic phase was washed with $H_2O$, brine, dried ($Na_2SO_4$) and concentrated. The residue was purified by flash chromatography to provide the desired acid as a colorless oil. $R_f$ 0.54, silica gel, $CH_2Cl_2$/MeOH/HOAc, 1/0.5/0.5.

This acid (0.65 g, 1.22 mmoles) was dissolved in $CH_2Cl_2$(6 ml), cooled to −15°, and treated successively with anisole (0.3 ml) and $CF_3CO_2H$ (5.7 ml). After 0.5 hr the solvent was removed and the residue purified by flash chromatography on silica gel eluting with MeOH/NH₄OH/H₂O, 10/0.4/0.4 to provide 58 as a white solid. $R_f$ 0.5, silica gel, MeOH/NH₄OH/H₂O, 10/1/1.

¹H NMR/300 MHz, (CD₃OD) δ0.88 (3H, t), 1.30 (5H, m), 1.62 (5H, m), 1.88 (2H, bd), 2.20 (2H, t), 2.89 (2H, m), 2.97 (2H, t), 3.30 (2H, m), 3.51 (2H, dd), 3.75 (4H, m).

Applicants hereby incorporate by reference procedures for preparing compounds of the present invention whereby guanidines are prepared from amines and whereby amidines are prepared from corresponding nitriles. Guanidines may be prepared from amines by those having ordinary skill in the art upon reaction with 3,5-dimethylpryazole-1-carboxamidine nitrate (*Methods Enzymol.*, 25b, 558, 1972). Amidines may be prepared from the corresponding nitrile by those having ordinary skill in the art of using procedures demonstrated by Boere, R. T., et. al. *J. Organomet Chem.*, 331(2), 161-7, 1987; and Fuks, R., *Tetrahedron*, 29 (14) 2147-51, 1973.

Applicants also incorporate by reference the procedure described in Repke et. al., Tetrahedron Letters (1979) pp. 4183-4184 for preparing N-alkylated glycines for glycine ethyl ester.HCl and the corresponding aldehyde or ketone in the presence of 10% Pd/C and hydrogen.

By means of the above methods, the following additional compounds were prepared.

| Compound | IC₅₀(μM) Inhibition of Platelet Aggregation |
|---|---|
| (1) Pib-N-(benzyl)Gly-3(R)-(2-phenethyl)-β-alanine | 0.25 |
| (2) Pib-N-(n-butyl)Gly-3(R)-(2-phenethyl)-β-alanine | 0.077 |
| (3) Pib-N-(i-Propyl)-3(R)-(2-phenethyl)-β-alanine | 0.099 |
| (4) Pib-N-(2-phenethyl)Gly-3(R)-(2-phenethyl)-β-alanine | 0.087 |
| (5) Pib-Gly-3(S)[2-(indol-3-yl)ethyl]-β-alanine ethyl ester | >1.0 |
| (6) Pib-Gly-3(S)-[2-(indol-3-yl)ethyl]β-alanine | 31 |
| (7) Pib-Gly-3,3-[2-phenethyl),(methyl)]β-alanine | >300 |
| (8) Pib-Gly-3-[2-(hydroxy)ethyl], β-alanine | >1.0 |
| (9) Pib-Gly-3-[4-(hydroxy)butyl], β-alanine | 3.7 |
| (10) Pib-Gly-3-(phenoxymethyl) β-alanine | 2.1 |
| (11) Pib-Gly-3-[2-(imidazol-4-yl)ethyl]β-alanine | 2.7 |
| (12) Pib-Gly-3-[2-(3-benzylimidazol-4-yl)ethyl]β-alanine | 1.5 |
| (13) Pib-Gly-3-(3-carboxypropyl) β-alanine | 4.0 |
| (14) Pib-Gly-3-[2-(2-methylindol-3-yl)ethyl]β-alanine | 1.1 |

Utilizing the methodology demonstrated in this invention, the following compounds, included in Table I below, are exemplary of the compounds, which may be prepared according to this invention.

TABLE I

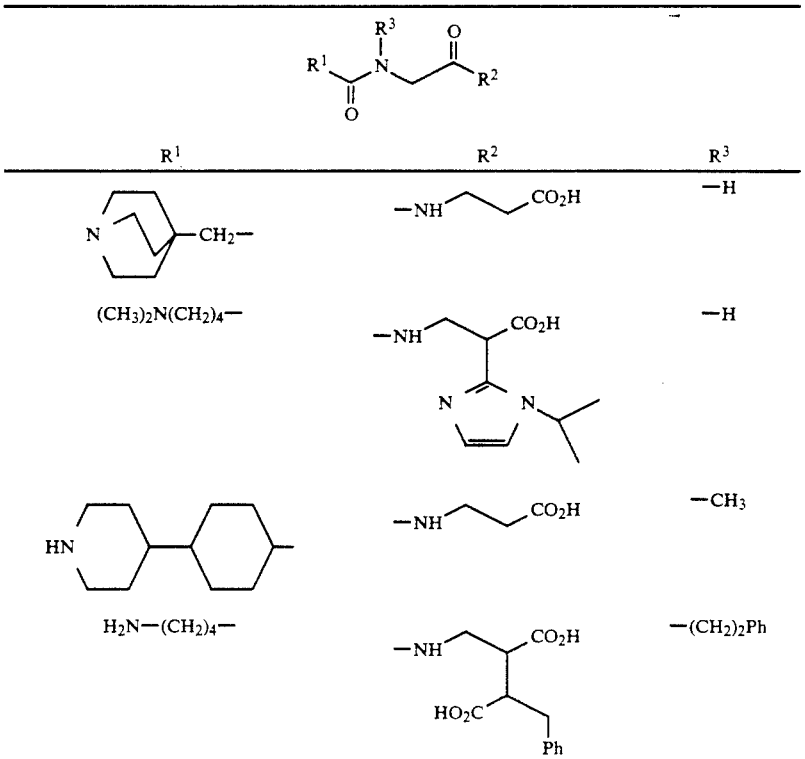

TABLE I-continued $$R^1-\underset{\underset{O}{\|}}{C}-\underset{R^3}{N}-CH_2-\underset{\underset{}{\|}}{C}(=O)-R^2$$

| R¹ | R² | R³ |
|---|---|---|
| PhCH₂NH(CH₂)₆— | —NH-CH₂-CH₂-CO₂H | —(CH₂)₂OH |
| (CH₃)HN-C(=NH)-NH—(CH₂)₂— | 3-(HO₂C-CH₂)-naphthyl-CH(NH—)-CH(CH₃)-CO₂H | —H |
| H₂N(CH₂)₄— | PhCH₂NH-C(=O)-CH₂-CH(NH—)-CH₂-CO₂H | —H |
| H₂N-CH₂-(4-C₆H₄)— | 4-HO-C₆H₄-CH(NH—CH₂-CO₂H)- (—NH-CH₂-CH(4-HO-C₆H₄)-CO₂H) | —C(CH₃)₃ |
| H₂N-C(=NH)-NH—(CH₂)₂— | naphthyl-O-C(=O)-CH(NH—)-CH₂-CO₂H | cyclohexyl-S— |
| NC-NH-C(=NH)-(3-C₆H₄)— | —NH-CH₂-CH₂-CO₂H | 4-Cl-cyclohexyl-O— |
| H₂N(CH₂)₄— | thienyl-CH₂-CH₂-CH(NH—)-CH₂-CO₂H | H |
| H₂N-CH₂-CH₂-S(=O)₂-CH₂-CH₃ | Ph-CH(NH—)-CH(CO₂H)-CH(CH₃)₂ | H |

TABLE I-continued

| R¹ | R² | R³ |
|---|---|---|
| H₂N-CH₂CH₂-S(O)₂-propyl | HO-CH(CO₂H)-CH(NH-)-CO₂H | —(CH₂)₃CO₂H |
| Ph-NH-CH₂-(cyclohexyl)-CH₂— | —NH-CH₂CH₂-CO₂H | H |
| H₂N(CH₂)₅— | PhO-CH₂-CH(NH-)-CO₂H | H |

What is claimed is:

1. A compound selected from the group consisting of: Pib-Gly-3[2-(2-methylindol-3-yl)ethyl]β-alanine, and Pib-Gly-3(R)-[2-(indol-3-yl)ethyl]β-alanine.

2. A composition for inhibiting the binding of fibrinogen to blood platelets in a mammal, comprising a compound of claim 1 and a pharmaceutically acceptable carrier.

3. A composition for inhibiting the aggregation of blood platelets in a mammal, comprising a compound of claim 1 and a pharmaceutically acceptable carrier.

4. A composition for preventing thrombus or embolus formation in a mammal, comprising a compound of claim 1 and a pharmaceutically acceptable carrier.

5. A composition for treating thrombus or embolus formation in a mammal, comprising a compound of claim 1 and a pharmaceutically acceptable carrier.

6. A method for inhibiting the binding of fibrinogen to blood platelets in a mammal, comprising administering to the mammal a composition of claim 3.

7. A method for inhibiting the aggregation of blood platelets in a mammal, comprising administering to the mammal the composition of claim 3.

8. A method for preventing thrombus or embolus formation in a mammal, comprising administering to the mammal the composition of claim 4.

9. A method for treating thrombus or embolus formation in a mammal, comprising administering to the mammal the composition of claim 5.

* * * * *